(12) United States Patent
Patel et al.

(10) Patent No.: US 8,247,775 B2
(45) Date of Patent: Aug. 21, 2012

(54) REMOTE OPTOTHERMAL SENSOR (ROSE) STANDOFF DETECTION OF CWAS, EXPLOSIVES VAPORS AND TICS

(76) Inventors: C Kumar N Patel, Los Angeles, CA (US); Anadi Mukherjee, Los Angeles, CA (US)

(*) Notice: Subject to any disclaimer, the term of this patent is extended or adjusted under 35 U.S.C. 154(b) by 1127 days.

(21) Appl. No.: 12/069,791

(22) Filed: Feb. 12, 2008

(65) Prior Publication Data
US 2012/0153156 A1 Jun. 21, 2012

(51) Int. Cl.
*G01J 5/02* (2006.01)
(52) U.S. Cl. .................................................. 250/341.1
(58) Field of Classification Search ............... 250/341.1
See application file for complete search history.

(56) References Cited

U.S. PATENT DOCUMENTS

| | | | | |
|---|---|---|---|---|
| 5,157,457 | A * | 10/1992 | Taylor | 356/480 |
| 6,853,452 | B1 * | 2/2005 | Laufer | 356/436 |
| 7,301,148 | B2 * | 11/2007 | Johnson | 250/338.4 |
| 2007/0210254 | A1 * | 9/2007 | Killinger et al. | 250/338.5 |

OTHER PUBLICATIONS

Department of the Army, *Army Field Manual No. 3-9; Potential Military Chemical/Biochemical Agents and Compounds*, pp. 19-20, Dec. 12, 1990.
B. McNamara and L. Leitnaker, "Toxicological Basis for Controlling Emission of GB into the Environment" *Edgewood Arsenal Special Publication*, (U.S. Army, Medical Research Laboratories, Edgewood Arsenal, Aberdeen Proving Grounds, Maryland) Mar. 1971.
Department of Health and Human Services, Center for Disease Control, "Final Recommendations for Protecting the Health and Safety Against Potential Adverse Effects of Long-Term Exposure to Low Doses of Agents: GA, GB, VX, Mustard Agent (H, HD and T) and Lewisite (L)", *Federal Register* 53, 8504-8507, Mar. 15, 1988.
Jimmie C. Oxley, James L. Smith, Kajal Shinde and Jesse Moran, "Determination of the Vapor Density of Triacetone Triperoxide (TATP) Using a Gas Chromatography Head Space Technique" *Propellants, Explosives, Pyrotechnics* 30, 127-130, 2005.
Ilya Dunayevskiy, Alexei Tsekoun, Manu Prasanna, Rowel Go and C. Kumar N. Patel "High Sensitivity Detection of Triacetone Triperoxide (TATP) and Its Precursor Acetone," *Applied Optics* 46, 6397-6404, 2007.
M. E. Webber, M. B. Pushkarsky and C. K. N. Patel, "Optical Detection of Chemical Warfare Agents and Toxic Industrial Chemicals: Simulation," J. Appl. Phys. 97, 113101, 2005.
M. B. Pushkarsky, M. E. Webber, T. Macdonald and C. K. N. Patel, "High Sensitivity, High Selectivity Detection of Chemical Warfare Agents." Appl. Phys. Lett. 88, 2006.
S. W. Sharpe, R. L. Sams, T.J. Johnson, P.M. Chu, G.C. Rhoderick and F. R. Guenther, "Creation of 0.10 $cm^{-1}$ Resolution, Quantitative, Infrared Spectral Libraries for Gas Samples," SPIE proceedings for Vibrational Spectroscopy-based Sensor Systems 4577, 12-24, 2001.
M. Lax, "Temperature Rise Induced by a Laser Beam," J. Appl. Phys. 48, 3919-3924, 1977.

(Continued)

*Primary Examiner* — David Porta
*Assistant Examiner* — Marcus Taningco
(74) *Attorney, Agent, or Firm* — Cislo & Thomas, LLP

(57) ABSTRACT

A system and method for standoff detection of explosives, CWAs and TICs using optical techniques. Preliminary analysis indicates detection of TNT at a distance of 0.5 km with a signal-to-noise ratio exceeding 10,000. The optical/thermal techniques apparently permit unambiguous detection of the target molecules even the presence of commonly encountered interferents. The technique, named Remote Optothermal Sensor (ROSE), has the potential for standoff detection at distances greater than one (1) kilometer.

22 Claims, 11 Drawing Sheets

OTHER PUBLICATIONS

CRC Handbook of Chemistry & Physics, 81st Edition, 2000-2001, p. 12-196.

D. O. Staley and G. M. Jurica, "Effective Atmospheric Emissivity under Clear Skies," J. Appl Meteorology 11, 249-356, 1972.

Michael Pushkarsky, Ilya Dunayevskiy, Manu Prasanna, Alexei Tsekoun, Rowel Go and C. Kumar N. Patel, "High-sensitivity Detection of TNT," Proc. Nat. Acad. Sciences 103, 19630-19634, 2006.

M. -C. Gagne and S.L. Chin, "Energy Relaxation Time in a Gas Mixture Measured by a Photothermal Probe Beam Deflection Technique," Appl. Phys. B 52, 352-358, 1991.

P. W. Kruse, "A Comparison of the Limits to the Performance of Thermal and Photon Detector Imaging Arrays," Infrared Phys. & Technol., 36, 869-882, 1995.

P. G. Datskos, N. V. Lavrik and S. Rajic, "Performance of Uncooled Microcantilever Thermal Detectors," Review of Scientific Instruments, 75, 1134-1148, 2004.

F. J. Crawford, "Electro-Optical Sensors Overview," IEEE AES Systems Magazine, 17-24, Oct. 1998.

Watson et al.; "Development and Application of Acute Exposure Guideline Levels (AEGLs) for Chemical Warfare Nerve and Sulfur Mustard Agents;" Journal of Toxicology and Environmental Health, Part B; online publication date Jul. 2008, pp. 1-93.

Army, Marine Corps, Navy, and Air Force Field Manual FM 3-11.9; Potential Miliary Chemical/Biological Agents and Compounds; pp. 1-318 (Jan. 2005).

C. Pflugl et al.; "Room-Temperature Continuous-Wave Operation of Long Wavelength (1=9.5mm) MOVEPE-frown Quantum Cascade Lasers;" Electronics Letters 43, pp. 1025-1026 (2007).

A. Lyakh et al.; "1.6 Watt, High Wallplug Efficiency, Continuous-Wave Room Temperature Quantum Cascade Laser Emitting at 4.6um;" Applied Physics Letters 92, 111110 (2008).

D. Weidmannn, et al.; "Mid-Infrared Trace-Gas Sensing with Quasi-Continuous-Wave Peltier-Cooled Distributed Feedback Quantum Cascade Laser;" Applied Physics B79, pp. 907-913 (2004).

G.Wysocki et al.; "Spectroscopic Trace-Gas Sensor with Rapidly Scanned Wavelengths of a Pulsed Quantum Cascade Laser for In-Situ NO Monitoring of Industrial Exhaust Systems;" Applied Physics B 80, pp. 617-625 (2005).

G. Wysocki, et al.; "Widely Tunable Mode-Hop Free External Cavity Quantum Cascade Laser for High Resolution Spectroscopic Applications;" Applied Physics B 81, pp. 769-777 (2005).

M. Pushkarsky, et al.; "Laser Based Photoacoustic Ammonia Sensors for Industrial Applications;" Applied Physics B 75, pp. 391-396 (2002).

M. Webber, et al.; "Agricultural Ammonia Sensor Using Diode lasers and Photoacoustic Spectroscopy;" Measurement Science and Technology 16, pp. 1547-1553 (2005).

A. Mukherjee, et al.; Sub-PPB Level Detection of Dimethyl Methyl Phosphonate (DMMP) Using Quantum Cascade Laser Photoacoustic Spectroscopy; Applied Optics 47, p. 1543 (2008).

A. Mandelis; "Photothermal Analysis of Thermal Properties of Solids;" J. Thermal Anal. 37, pp. 1065-1101 (1991).

K. Cottingham; "Ion Mobility Spectrometry Rediscovered;" Product Review, Analytical Chemistry; Oct. 1, p. 435A (2003).

A. Kanu, et al.; "Special Feature: Perspective on Ion Mobility-Mass Spectrometry;" J. of Mass Spectrometry 43, pp. 1-22 (2008).

R. Ewing et al.; "A Critical Review of Ion Mobility Spectrometry for the Detection of Explosives and Expolsive Related Compounds;" Talanta 54, pp. 515-529 (2001).

Internet Site: Smith Detection; (www.geindustrial.com/geinterlogix/iontrack); Vapor Tracer from GE Industrial, "IONSCAN 400B".

C.Van Neste, et al.; "Surface Photoacoustic Spectroscopy;" Applied Physics Letters 92, 234012 (2008).

G. Guizetti, et al.; Handbook of optical Constants of Solids; "Lead Sulfide;" Academic Press, 1988, Ed. Edward D. Palik, (5 sheets).

Internet Site: Wolfram Research (www.wolfram.com); "The Transcendental Equation (18) Can Be Solved Using Mathematica 5;".

F. Pristera, et al,; "Analysis of Explosives Using Infrared Spectroscopy;" Anal. Chem, 32, pp. 495-508 (1960).

Department of Health and Human Services, Center for Disease Control; "Final Recommendations for Protecting Health from Potential Adverse Effects of Exposure to Agents GA (Taburn), GB (Sarin), and VX;" Federal Register vol. 68, pp. 58348-58351 (Oct. 9, 2003).

* cited by examiner $$
\begin{vmatrix} \alpha_{\lambda_1,1} & \alpha_{\lambda_1,2} & \cdots & \alpha_{\lambda_1,M} \\ \alpha_{\lambda_2,1} & \alpha_{\lambda_2,2} & \cdots & \alpha_{\lambda_2,M} \\ \vdots & \vdots & \ddots & \vdots \\ \alpha_{\lambda_N,1} & \alpha_{\lambda_N,2} & \cdots & \alpha_{\lambda_N,M} \end{vmatrix} \begin{vmatrix} X_1 \\ X_2 \\ \vdots \\ X_M \end{vmatrix} = K \times \begin{vmatrix} \Delta T_{\lambda_1} \\ \Delta T_{\lambda_2} \\ \vdots \\ \Delta T_{\lambda_N} \end{vmatrix}
$$

*Spectral Coefficients*     *Mole fractions*     *Measured Temperature*

Figure 4

REMOTE OPTOTHERMAL SENSOR (ROSE) STANDOFF DETECTION OF CWAS, EXPLOSIVES VAPORS AND TICS

COPYRIGHT AUTHORIZATION

A portion of the disclosure of this patent document contains material which is subject to copyright and/or mask work protection. The copyright and/or mask work owner has no objection to the facsimile reproduction by anyone of the patent document or the patent disclosure, as it appears in the Patent and Trademark Office patent file or records, but otherwise reserves all copyright and/or mask work rights whatsoever.

BACKGROUND OF THE INVENTION

1. Field of the Invention

This invention relates to the detection of gasses at long distance and more particularly the detection of hazardous or chemical weapon gasses by detection of optical response.

2. Description of the Related Art

Chemical warfare agents (CWAs), explosives vapors and many toxic industrial chemicals (TICs) absorb radiation in the medium wave infrared (MWIR) and long wave infrared (LWIR) region. This is the basis of high sensitivity, high selectivity low probability of false alarm (PFA) detection of these targets using to make MWIR and LWIR laser photoacoustic spectroscopy (L-PAS). L-PAS is a point sensor system. The method and technology of using tunable IR lasers, photoacoustic spectroscopy sensitivity and calculation of receiver operational characteristic (ROC) curve have been described in a number of papers and/or publications by the inventors and their colleagues at Pranalytica, Inc. of Santa Monica, Calif. (incorporated herein by reference).

For single-ended standoff detection applications, traditional light detection and ranging (LIDAR) and differential absorption LIDAR (DIAL) measurement schemes are less than satisfactory because of the small Raman scattering signal returns (for LIDAR) and small Rayleigh scattering returns (for DIAL) from molecular clouds containing explosives vapors and CWAs, especially when the target gasses are present at low concentrations. On the other hand, for a CWA gas cloud containing explosives vapors or CWAs even at ppm concentrations, the infrared absorption coefficients are large enough (in the range of $10^{-2}$ to $10^{-3}$ $m^{-1}$ at 1 ppm concentration) to detect their presence, if the cloud dimensions are reasonably large (tens to hundreds of meters), as would be the case, for example, for intentional release of a chemical warfare agent. Table 1 gives typical numbers for Raman scattering, Rayleigh scattering and infrared absorption cross-sections. An initial choice of 1 ppm target may be selected from the consideration of human sensitivity to Sarin exposure of which varies from 17 ppm for lethality [1] to 170 ppb for miosis [2] for a one minute exposure. Furthermore, for a standoff detection of triacetone triperoxide (TATP), 1 ppm of vapor pressure corresponds to a TATP temperature of −5° C. [3,4].

TABLE 1

Typical values for Raman scattering, Rayleigh scattering and infrared absorption cross-sections (note that numbers may vary by 1-2 orders of magnitude depending on the specific molecular species)

| Process | Cross-Section |
| --- | --- |
| Raman scattering | $\sim 10^{-30}$ $cm^2$ $molecule^{-1}$ |
| Rayleigh scattering | $\sim 10^{-28}$ $cm^2$ $molecule^{-1}$ |
| Infrared absorption | $\sim 10^{-17}$ $cm^2$ $molecule^{-1}$ |

Infrared absorption measurements are the basis of the L-PAS sensors that are able to detect CWAs at ppb levels in a path length of 10 cm (point sensor). Point detection of TATP at vapor pressures down to about 1 ppb corresponding to a TATP temperature of −45° C. using laser photoacoustic spectroscopy is known [4]. Thus, measuring absorption rather than scattering appears to be more important for standoff detection. Of course, if a double-ended system were to be acceptable, standoff detection of tens of meters of a CWA cloud would be straightforward. However, for a single-ended detection scheme, the problem is significantly harder and provides significant additional obstacles.

Known CWAs include: Cyclosarin (GF), Sarin (GB), Soman (GD), Tabun (GA), VX, some insecticides, Novichok agents, most arsines, cyanogen chloride, hydrogen cyanide, sulfur mustard (HD, H), nitrogen mustard (HN-1, HN-2, HN-3), Lewisite (L), Phosgene oxime (CX), chlorine, hydrogen chloride, nitrogen oxides, phosgene, tear gas, pepper spray, Agent 15 (BZ), and non-living biological proteins such as ricin and abrin. The foregoing list is not complete, but gives an indication of the types of chemicals that are used as chemical warfare agents (CWAs). Similar lists are known for explosives and/or explosives vapors as well as toxic industrial chemicals (TICs).

One such list for TICs is available through OSHA (the U.S. Department of Labor's Occupational Safety & Health Administration). OSHA maintains a web site listing TICs at the URL http://www.osha.gov/SLTC/emergencypreparedness/guides/chemical.html which indicates as follows:

Toxic industrial chemicals are industrial chemicals that are manufactured, stored, transported, and used throughout the world. Toxic industrial chemicals can be in the gas, liquid, or solid state. They can be chemical hazards (e.g., carcinogens, reproductive hazards, corrosives, or agents that affect the lungs or blood) or physical hazards (e.g., flammable, combustible, explosive, or reactive). The following table lists the most common TICs listed by their hazard index.

| TICs listed by hazard index | | |
| --- | --- | --- |
| High | Medium | Low |
| Ammonia | Acetone cyanohydrin | Allyl isothiocyanate |
| (CAS# 7664-41-7) | (CAS# 75-86-5) | (CAS# 57-06-7) |
| Arsine | Acrolein | Arsenic trichloride |
| (CAS# 7784-42-1). | (CAS# 107-02-8) | (CAS# 7784-34-1) |
| Boron trichloride | Acrylonitrile | Bromine |
| (CAS# 10294-34-5) | (CAS# 107-13-1) | (CAS# 7726-95-6) |
| Boron trifluoride | Allyl alcohol | Bromine chloride |
| (CAS# 7637-07-2) | (CAS# 107-18-6) | (CAS# 13863-41-7) |
| Carbon disulfide | Allylamine | Bromine pentafluoride |
| (CAS# 75-15-0) | (CAS# 107-11-9) | (CAS# 7789-30-2) |
| Chlorine | Allyl chlorocarbonate | Bromine trifluoride |
| (CAS# 7782-50-5) | (CAS# 2937-50-0) | (CAS# 7787-71-5) |
| Diborane | Boron tribromide | Carbonyl fluoride |
| (CAS# 19287-45-7) | (CAS# 10294-33-4) | (CAS# 353-50-4) |
| Ethylene oxide | Carbon monoxide | Chlorine pentafluoride |
| (CAS# 75-21-8) | (CAS# 630-08-0) | (CAS# 13637-63-3) |

-continued

| TICs listed by hazard index | | |
|---|---|---|
| Fluorine (CAS# 7782-41-4) | Carbonyl sulfide (CAS# 463-58-1) | Chlorine trifluoride (CAS# 7790-91-2) |
| Formaldehyde (CAS# 50-00-0) | Chloroacetone (CAS# 78-95-5) | Chloroacetaldehyde (CAS# 107-20-0) |
| Hydrogen bromide (CAS# 10035-10-6) | Chloroacetonitrile (CAS# 7790-94-5) | Chloroacetyl chloride (CAS# 79-04-9) |
| Hydrogen chloride (CAS# 7647-01-0) | Chlorosulfonic acid (CAS# 7790-94-5) | Crotonaldehyde (CAS# 123-73-9) |
| Hydrogen cyanide (CAS# 74-90-8) | Diketene (CAS# 674-82-8) | Cyanogen chloride (CAS# 506-77-4) |
| Hydrogen fluoride (CAS# 7664-39-3) | 1,2-Dimethylhydrazine (CAS# 540-73-8) | Dimethyl sulfate (CAS# 77-78-1) |
| Hydrogen sulfide (CAS# 7783-0604) | Ethylene dibromide (CAS# 106-93-4) | Diphenylmethane-4,4'-diisocyanate (CAS# 101-68-8) |
| Nitric acid, fuming (CAS# 7697-37-2) | Hydrogen selenide (CAS# 7783-07-5) | Ethyl chlroroformate (CAS# 541-41-3) |
| Phosgene (CAS# 75-44-5) | Methanesulfonyl chloride (CAS# 124-63-0) | Ethyl chlorothioformate (CAS# 2941-64-2) |
| Phosphorus trichloride (CAS# 7719-12-2) | Methyl bromide (CAS# 74-83-9) | Ethyl phosphonothioic dichloride (CAS# 993-43-1) |
| Sulfur dioxide (CAS# 7446-09-5) | Methyl chloroformate (CAS# 79-22-1) | Ethyl phosphonic dichloride (CAS# 1066-50-8) |
| Sulfuric acid (CAS# 7664-93-9) | Methyl chlorosilane (CAS# 993-00-0) | Ethyleneimine (CAS# 151-56-4) |
| Tungsten hexafluoride (CAS# 7783-82-6) | Methyl hydrazine (CAS# 60-34-4) | Hexachlorocyclo-pentadiene (CAS# 77-47-4) |
| | Methyl isocyanate (CAS# 624-83-9) | Hydrogen iodide (CAS# 10034-85-2) |
| | Methyl mercaptan (CAS# 74-93-1) | Iron pentacarbonyl (CAS# 13463-40-6) |
| | Nitrogen dioxide (CAS# 10102-44-0) | Isobutyl chloroformate (CAS# 543-27-1) |
| | Phosphine (CAS# 7803-51-2) | Isopropyl chloroformate (CAS# 108-23-6) |
| | Phosphorus oxychloride (CAS# 10025-87-3) | Isopropyl isocyanate (CAS# 1795-48-8) |
| | Phosphorus pentafluoride (CAS# 7647-19-0) | n-Butyl chloroformate (CAS# 592-34-7) |
| | Selenium hexafluoride (CAS# 7783-79-1) | n-Butyl isocyanate (CAS# 111-36-4) |
| | Silicon tetrafluoride (CAS# 7783-61-1) | Nitric oxide (CAS# 10102-43-9) |
| | Stibine (CAS# 7803-52-3) | n-Propyl chloroformate (CAS# 109-61-5) |
| | Sulfur trioxide (CAS# 7446-11-9) | Parathion (CAS#: 56-38-2) |
| | Sulfuryl fluoride (CAS# 2699-79-8) | Perchloromethyl mercaptan (CAS# 594-42-3) |
| | Tellurium hexafluoride (CAS# 7783-80-4) | sec-Butyl chloroformate (CAS# 17462-58-7) |
| | n-Octyl mercaptan (CAS# 111-88-6) | tert-Butyl isocyanate (CAS# 1609-86-5) |
| | Titanium tetrachloride (CAS# 7550-45-0) | Tetraethyl lead (CAS# 78-00-2) |
| | Tricholoroacetyl chloride (CAS# 76-02-8) | Tetraethyl pyrophosphate (CAS# 107-49-3) |
| | Trifluoroacetyl chloride (CAS# 354-32-5) | Tetramethyl lead (CAS# 75-74-1) |
| | | Toluene 2,4-diisocyanate (CAS# 584-84-9) |
| | | Toluene 2,6-diisocyanate (CAS# 91-08-7) |

Some of the foregoing OSHA-listed TICs may be either gasses or subject to aerosolization.

SUMMARY OF THE INVENTION

In view of the foregoing disadvantages inherent in the known methods of detecting gasses (from a single point or otherwise) now present in the prior art, the present invention provides a new method of detecting hazardous, chemical warfare, explosives vapors, or other gasses by detection of optical response wherein the same can be utilized for detecting gasses at long distance and more particularly the detection of hazardous or weapon gasses by detection of optical response at a distance.

The general purpose of the present invention, which will be described subsequently in greater detail, is to provide a new method and system by which gasses and constituent molecules may be analyzed at a safe distance which has many of the advantages of prior detectors and many novel features that result in a new gas detector which is not anticipated, rendered obvious, suggested, or even implied by any of the prior art detectors, either alone or in any combination thereof.

A "stand-off" system of detection of CWAs, explosives vapors and TIC clouds with high sensitivity, low PFA and high selectivity is set forth herein. The technology involves using photothermal spectroscopy at a distance rather than photoacoustic spectroscopy in a point sensor local to the sample, although the underlying principles of the two techniques are similar. CWA detection as well as explosives vapors detection at standoff distances of 500 m to 2 km may be possible. Prospective and/or prophetic examples are provided, below.

In one embodiment of the present invention, a system for the remote detection of gasses uses a laser tuned to a first wavelength of interest for a first gas. The laser is adapted for illuminating (from a distance) a cloud of gas. A heat sensor is used that is adapted for detecting heat generated by a gas absorbing the first wavelength. In this way, the first gas is detectable in a gas cloud by illuminating the gas cloud with the first wavelength and by detecting heat generated or radiated by the first gas with the heat sensor. Additional embodiments expand upon this process so that several gasses can be determined in a very short period of time by the serial (or otherwise) illumination of the gas cloud by several wavelengths.

In another embodiment of the present invention, a method for determining the constituents of a gas cloud with possibly several unknown components is set forth. The steps of the inventive method include providing a source of illumination capable of transmitting a plurality of wavelengths and illuminating the gas cloud with only one illuminating wavelength at a time from the source. Determination of an optical response of the gas cloud to each illuminating wavelength is made resulting in the determination of the constituent gasses of the gas cloud by resolving a mole fraction for each constituent. In this way, the constituents and their degree of presence/percentage of the gas cloud are determined.

BRIEF DESCRIPTION OF THE APPENDICES

The following appendices are incorporated herein by this reference thereto.

Appendix 1 is a table showing commercially available compact telescopes

Appendix 2 is a table showing commercially available infrared imaging systems.

Appendix 3 is a list of references corresponding to the bracketed numbers used herein.

BRIEF DESCRIPTION OF THE DRAWINGS

FIG. 4 is a matrix equation using the principle of extracting mole fractions of target gasses from measured temperature rise of the gas column and laboratory data of the absorption coefficients of the constituent gasses. K is an experimentally determined constant that includes camera/telescope parameters, etc. that can be determined using this same equation under known circumstances.

DESCRIPTION OF THE PREFERRED EMBODIMENT(S)

Figure 1:
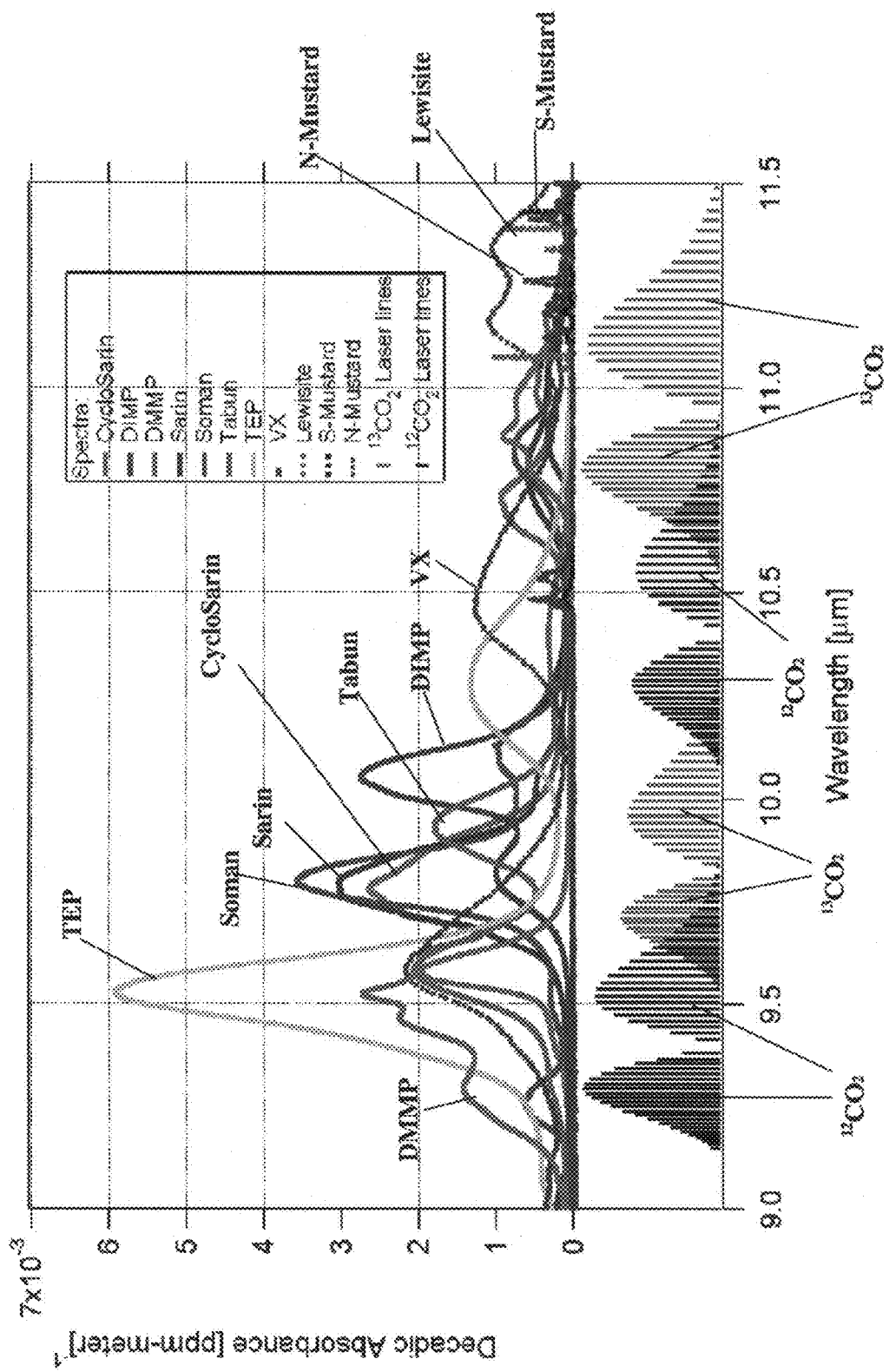
FIG. 1 is a graphical representation of infrared absorption fingerprints of a number CWAs in the 9-11.5 μm region (top); Positions of $^{12}CO_2$ and $^{13}CO_2$ laser lines (bottom).

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

The present invention resides in a novel system and method for standoff detection of explosives, CWAs and TICs using optical techniques. Preliminary analysis indicates that TNT can be detected at a distance of 0.5 km with a signal-to-noise ration exceeding 10,000. Optical techniques may permit unambiguous detection of target molecules even in the presence of commonly-encountered interferents. The technique, named Remote Optothermal Sensor (ROSE), has the potential for standoff detection at distances greater than one (1) kilometer.

Referring to the drawings, where like numerals of reference designate like elements throughout, it will be noted that in implementing the present invention, a remote cloud containing CWAs, explosives with high vapor pressure such as TATP, and/or TICs, may be illuminated at specific infrared (or other) wavelengths that are characteristic absorption wavelengths of the targets. The resulting temperature rise of the illuminated column may be measured remotely with a sensitive infrared sensor. By measuring the resulting temperature rises for corresponding wavelengths, the presence and relative percentage of the remote cloud's constituents can be obtained (with a sufficient number of measurements). The laser wavelength may be tuned to select a target gas/vapor and may discriminate against interferents by using a multiplicity of illuminating wavelengths as has been demonstrated with laser photoacoustic spectroscopy (L-PAS) [5, 6].

By illuminating a remote cloud of the target gas (CWA, explosives vapors, and/or TICs) with a tunable IR laser whose tuning range overlaps with IR absorption bands of the target, unique spectral responses can be induced, elicited, and/or caused. These spectral responses can then be discriminatingly detected. For illustrative purposes, focus is made on CWAs as the target gasses. FIG. 1 shows the strong absorption features of several CWA's and the positions of $^{12}CO_2$ laser and $^{13}CO_2$ laser lines in the lower panel. The absorbances of almost all of the CWAs lie in the range of $3\text{-}6\times10^{-3}$ (ppm·meter)$^{-1}$, which translate into absorption coefficients in the range of $7\times10^{-3}$ to $1.4\times10^{-2}$ (ppm·meter)$^{-1}$. Thus a cloud of dimension 70-140 meters and a concentration of 1 ppm of the target gas will absorb ~67% of the laser radiation at the peak of the absorption feature. The next challenge is to detect this absorbed radiation remotely.

Figure 2:
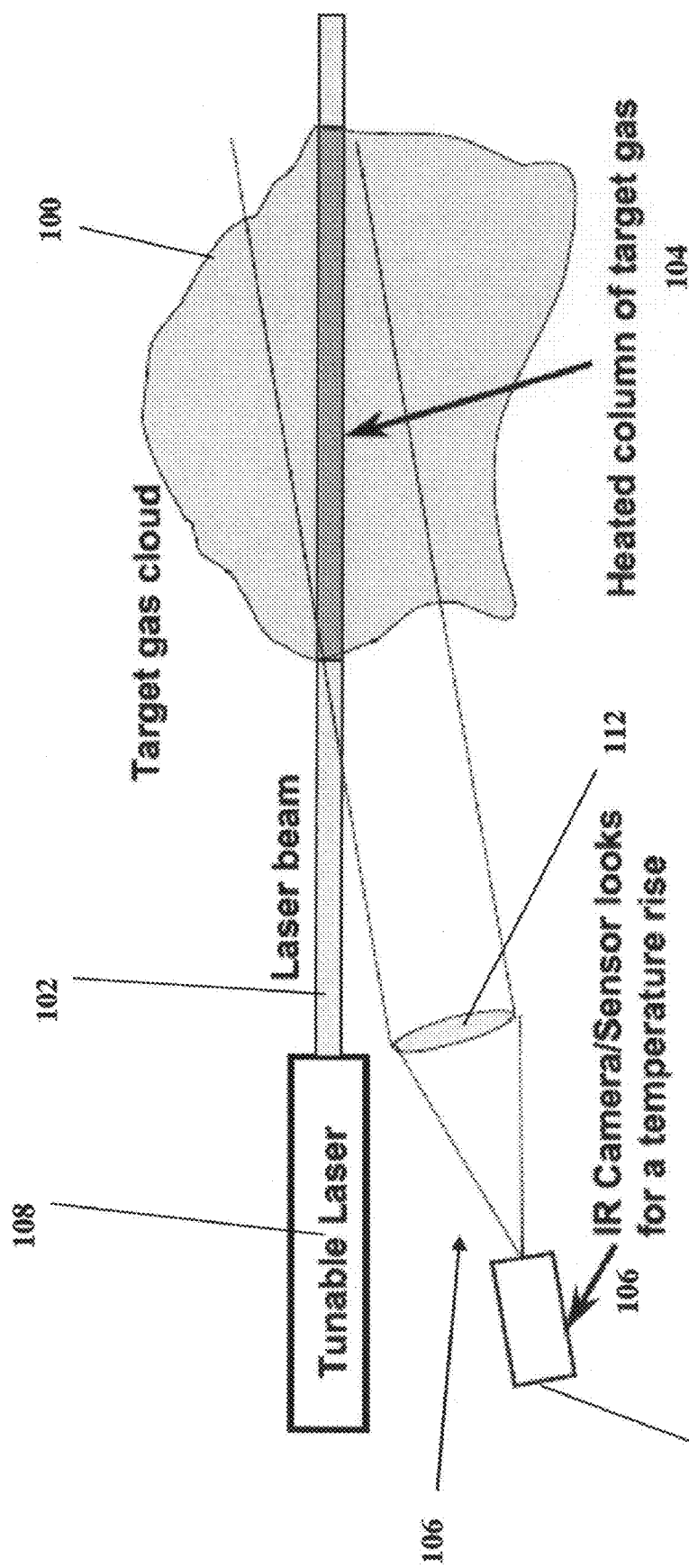
FIG. 2 is a schematic of the Remote Optothermal Sensor (ROSE) for standoff detection of explosives vapors, CWAs and TICs.

An experimental equipment schematic is shown in FIG. 2 and involves illuminating a target gas cloud 100 with a laser beam 102 that is absorbed by the target gas 100. The absorption of the laser radiation causes the target gas cloud to heat up in the form of an illuminated column 104.

The temperature rise of the column 104 will cause the column 104 to radiate as a black body with emissivity that is characteristic of the composition of the gas cloud 100 at a temperature higher than that of the surrounding gas, which is generally in thermal equilibrium with ambient. The IR camera/telescope combination 106 is designed to look at the column 104 that is illuminated by the tunable laser 108 and therefore will see the column temperature as being higher than that of the rest of the cloud 100. The temperature rise can be quantitatively measured from this remote camera 110. In the infrared spectral region, most if not all of the molecules, especially large molecules of the target gasses, relax after being excited by the laser radiation through very rapid conversion of the absorbed energy into translational energy of the molecules, i.e., a temperature rise of the gas. This is the mechanism that makes photoacoustic spectroscopy work. Furthermore, if there is no absorption in the illuminated region, there is no heating of the gas cloud.

The temperature rise ΔT is proportional to the total absorbed energy (from the laser beam) by the target gas cloud, $$\Delta T \propto P_{in}(1-e^{-\alpha l}) \qquad (1)$$

where $P_{in}$ is the laser power incident on the cloud, α is the absorption coefficient of the target gas at the particular laser wavelength and l is the cloud dimension along the excited column. The heated gas column will be at a temperature higher than its surroundings. As described below, a typical temperature rise, ΔT, of a few degrees C. is expected. As to be expected, use of a higher power laser would generally result in a higher temperature rise.

For the purposes of evaluating the feasibility of remote photothermal detection, the detection of a "cloud" that has been seeded with 1 ppm of $SF_6$ is described herein. The description of operations given herein are prospective and/or prophetic in nature and do not reflect actual experiments unless otherwise indicated. Sulfur hexafluoride ($SF_6$) may be used as a surrogate for CWA/explosives vapors because it has a strong and well defined infrared absorption feature near 10.55 μm, much like the absorption features of many CWAs. Moreover, $SF_6$ is a relatively inert and benign gas, a feature that facilitates experimental optimization of the remote photothermal sensing technology without having to deal with real (and extremely dangerous) CWAs in the early stages of R&D activities. Testing with real CWAs may be carried out subsequently at appropriate government facilities.

FIG. 3 shows the infrared "fingerprint" absorption spectrum of $SF_6$ near 10.55 μm obtained from the PNNL database [7]. Locations of $^{12}CO_2$ laser lines are also shown by the indicating dots. For initial calculations and experimentation, the 10P(16) transition of the $^{12}CO_2$ laser for illuminating the gas cloud is used. After the $SF_6$ cloud has absorbed the $CO_2$ laser radiation, there will be a local rise in temperature due to thermal relaxation of the molecules with its gaseous environment. The absorbed laser light is converted into heat. The average collisional time at atmospheric pressure is ~300 ps. Intramolecular relaxation time through the vibrational-rotational manifold within the same electronic state for a complex molecule is ~μs (on the order of microseconds). So, the $SF_6$ molecules predominantly relax through intermolecular collisions. The time for complete relaxation of the radiatively excited molecules to translational energy of the surrounding gas (i.e., conversion to heat) is estimated to be less than a few μs. In essence, the excited $SF_6$ molecules lose their internal vibrational energy and heat up the gas volume very rapidly.

Hot gasses behave like blackbody radiators with finite emissivity. In order to calculate the energy radiated by the $SF_6$ cloud from Stefan-Boltzmann law, the temperature rise of the cloud in which the column of $SF_6$ is excited and the emissivity of the gas mixture comprising the cloud must be known. Since $SF_6$ is a minor constituent of the gas mixture (1 ppm), the emissivity will be determined primarily by the carbon dioxide and water content of the ambient air cloud.

With a sensitive infrared detector or camera, the detection part could be assured (see the calculations below) because of the strong absorption by the target gasses, all the CWAs and vapors of explosives, whose typical absorption coefficient, α, is $10^{-2}$-$10^{-3}$ $(\text{ppm}\cdot\text{meter})^{-1}$ as seen from FIG. 1. Therefore a cloud of gas 10-100 meters long would absorb as much as 10-50% of the laser radiation at the peak of the absorption feature. The sensitivity calculations are also presented below.

However, it should be emphasized that the presence of the target gas in a real environment (and not in clean dry air) where more than one target gas may be present and where interferents, which could absorb radiation of the same laser wavelength as that absorbed by the target molecule, may also be present. Thus, the measured ΔT will generally have contributions from other gasses that absorb at the same laser wavelength. That is, the coefficient of absorption of the cloud itself at a certain wavelength, $\alpha_{\lambda_i}$ is $$\alpha_{\lambda_i} = \sum_{j=1}^{n} \alpha_j, \lambda_i \tag{2}$$

where $\alpha_{j,\lambda_i}$ is the absorption coefficient of the $j^{th}$ component of the cloud at the wavelength $\lambda_i$.

$$\therefore \Delta T_{\lambda_i} \propto \sum_{j=1}^{n} \alpha_j, \lambda_i \tag{3}$$

This is very reminiscent of the L-PAS scheme [5,6] where the photoacoustic signal at $\lambda_i$ is proportional to the sum total of absorption caused by all the components of the gas sample in the photoacoustic cell at the wavelength $\lambda_i$.

In order to identify any specific target gas with selectivity and low PFA, the column temperatures, $\Delta T_{\lambda_i}$, at a number of wavelengths covering the absorption features of the target gas cloud need to be measured. Thus, there are $$\Delta T_{\lambda_1}, \Delta T_{\lambda_2}, \Delta T_{\lambda_3} m \ldots \Delta T_{\lambda_n} \tag{4}$$

each one of which is proportional to the sum total of absorption caused by various components at the relevant wavelength.

By knowing the laboratory values of $\alpha_{j,\lambda_i}$, the matrix can be inverted (requiring the spectral coefficient matrix to be a square matrix, thus making N=M herein) and concentrations of individual target gasses as well as those of the interferents can be obtained. From these data, a receiver operation characteristic (ROC) curve can be deduced for the target using the phenomenology developed earlier by replacing the photoacoustic signal, $S_{\lambda_i}$, with the measured $\Delta T_{\lambda_i}$ at various wavelengths [5,6]. Since the stand off detection system herein enjoys some similarities with L-PAS, good sensitivity with low PFA should be obtained. As shown in the matrix equation of FIG. 4 and equation (5), below, the values of $\alpha_{j,\lambda_i}$ are measured and obtained from the lab while the values of $\Delta T_{\lambda_i}$ are measured in the field. Therefore, the mole fractions of each of the components in the gas cloud can be determined. Here K is the experimentally determined constant that includes the camera/telescope parameters and the overlap of the field of view (FOV) of the telescope 112 and the gas column illuminated by the laser beam 104 that can be determined using this same equation under known circumstances.

$$\underbrace{\begin{vmatrix} \alpha_{\lambda_1,1} & \alpha_{\lambda_1,2} & \cdots & \alpha_{\lambda_1,M} \\ \alpha_{\lambda_2,1} & \alpha_{\lambda_2,2} & \cdots & \alpha_{\lambda_2,M} \\ \vdots & \vdots & \vdots & \vdots \\ \alpha_{\lambda_N,1} & \alpha_{\lambda_N,2} & \cdots & \alpha_{\lambda_N,M} \end{vmatrix}}_{\text{Spectral Coefficients}} \underbrace{\begin{vmatrix} X_1 \\ X_2 \\ \vdots \\ X_M \end{vmatrix}}_{\text{Mole fractions}} = K \times \underbrace{\begin{vmatrix} \Delta T_{\lambda_1} \\ \Delta T_{\lambda_2} \\ \vdots \\ \Delta T_{\lambda_N} \end{vmatrix}}_{\text{Measured Temperature}} \tag{5}$$

As shown in FIG. 4 and matrix equation (5), above, the mole fractions of target gasses are determined from the measured temperature rises of the gas column at wavelength ($\Delta T_{\lambda_i}$) and laboratory data of the absorption coefficients of the constituent gasses $\alpha_{\lambda di\ i,j}$. K, per above, is an experimentally determined constant that includes camera/telescope parameters, etc. Note should be taken that the index M is the same for the absorption coefficients and the mole fractions. For every unknown mole fraction to be determined, an illumination of the gas cloud at a unique wavelength is made. While the mole fractions of nitrogen ($N_2$), oxygen ($O_2$), carbon dioxide ($CO_2$), and water ($H_2O$) may be known, it may also be useful to treat these primary constituents of air as unknowns for the determinations to be made via equation (5).

Per above, K could be resolved under controlled circumstances by using known concentrations of responsive gasses in the wavelength regime of interest. The measured temperatures may then be divided into the matrix product of the spectral coefficients and the mole fractions to determine K.

Feasibility Calculations for Standoff Detection of a Target Gas Cloud

Figure 3:
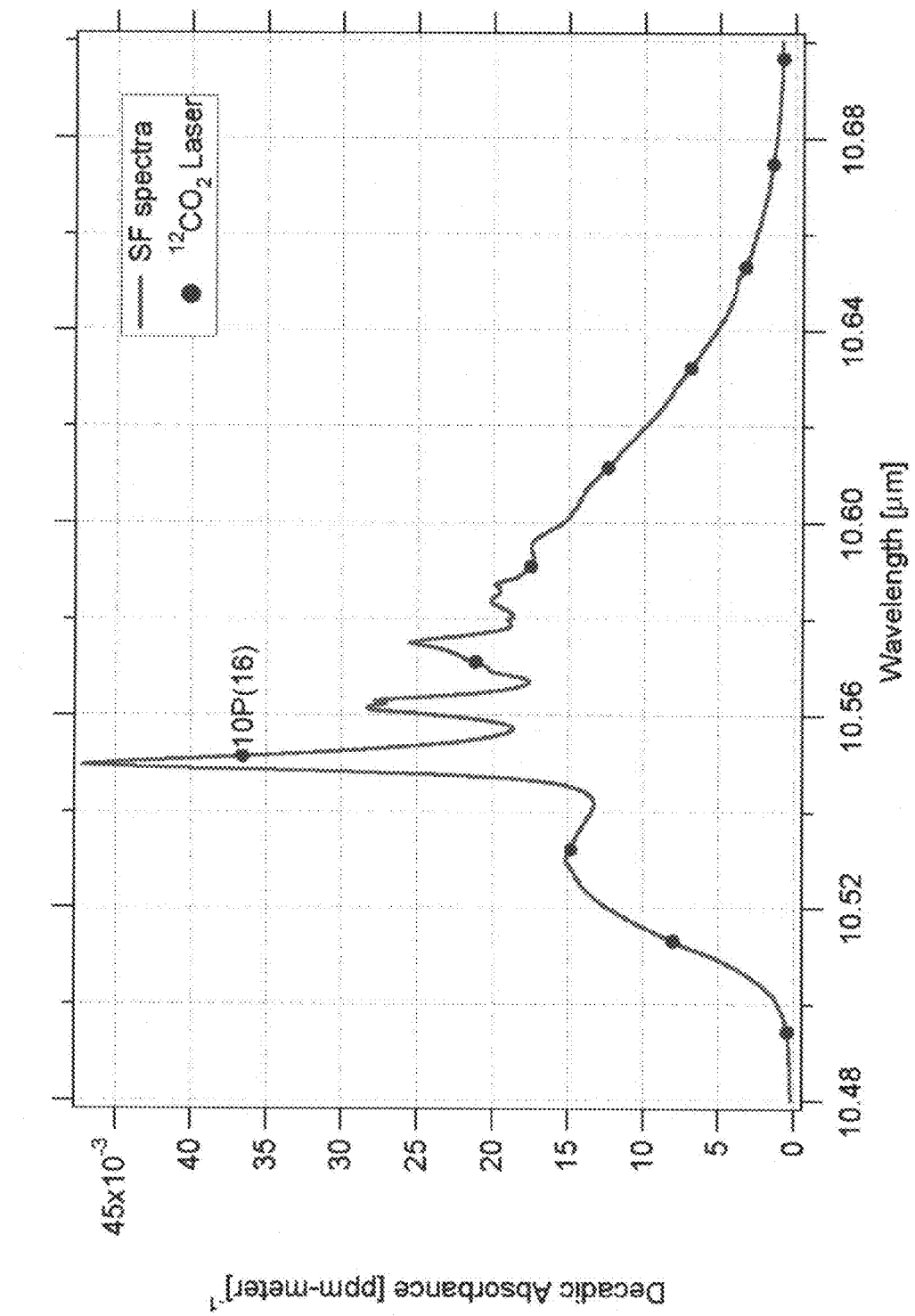
FIG. 3 shows graphically an infrared absorption fingerprint of $SF_6$ in the 10.5 μm region. Locations of $^{12}CO_2$ laser lines are also shown.

As an illustrative example, calculation may be carried out for the detection of a cloud of $SF_6$ released at some distance and having an average concentration of 1 ppm in the atmospheric "cloud." $SF_6$ has a characteristic absorption feature at ~10.55 μm as seen in FIG. 3, and is relatively benign for initial demonstration purposes. The cloud of $SF_6$ exposed to a $CO_2$ laser beam should be heated up spatially and temporally. The challenge is to detect the thermal emission of $SF_6$ in the cloud using an IR camera (or a sensor) placed at a distance (typically >50 meters) with high sensitivity and selectivity.

This problem may be addressed by using the following procedure (given for purposes of example and not for those of limitation):

(1) Calculate steady state maximum temperature rise of a highly absorbing target when exposed to a 1 Watt $CO_2$ laser beam of spot size 1 cm;

(2) Calculate steady state maximum temperature rise in a $SF_6$ cloud that has distributed absorption;

(3) Determine time dependent behavior of laser induced heating of gas;

(4) Accommodate choices of LWIR cameras and lenses;

(5) Image the blackbody radiated power on the IR camera;

(6) Determines detection sensitivity of IR camera and gas detection sensitivity; and (7) Determine response times of IR cameras—phase sensitive detection.

Calculation of the Temperature Rise

To know the temperature rise of the $SF_6$ cloud, the heat equation in this particular case needs to be analyzed. The heat equation can be written as:

$$C\frac{\partial T}{\partial t} = -\mathrm{div} J + E \tag{6}$$

where T is the temperature, C is the heat capacity, J is the flux of heat flow and E is the laser energy absorbed per unit volume per second (source term). Here, $J=-K\nabla T$, where K is the thermal conductivity. Thus, equation (6) takes the form of a regular diffusion equation:

$$\nabla^2 T = \frac{1}{\kappa}\frac{\partial T}{\partial t} - \frac{E}{K} \tag{7}$$

where the thermal diffusivity $\kappa=K/C=K/\rho c$, where $\rho$ is the density and c is the specific heat per unit mass. Solution of equation (7) holds all the information we need both in steady state (laser not chopped) and time dependent (chopped laser) cases.

Steady State Case

In the steady-state, equation (7) reduces to Poisson's equation:

$$\nabla^2 T = -\frac{E}{K} \tag{8}$$

The energy absorbed per unit volume per second is $E=\text{intensity}\times\text{absorption}=I\times e^{-\alpha z}$, where I is the Gaussian intensity of the laser beam $I=I_0 e^{-(r^2/w^2)}$, z is the depth coordinate, r is the radial coordinate and w is the beam spot size. Using the radial (i.e., cylindrical) symmetry of Gaussian laser beams, equation (8) can be solved by Bessel transform. The complete solution of equation (8) has been given by Lax [8]:

$$T(R, Z, W) = B \int_0^\infty J_0(\lambda R) F(\lambda) \frac{W e^{-\lambda z} - \lambda e^{-Wz}}{W^2 - \lambda^2} d\lambda \tag{9}$$

where the dimensionless parameters are R=r/w, Z=z/w, W=αw, $B=\alpha P/2\pi K F(0)$ and P=total incident power of the laser beam. The Gaussian function $F(R)=e^{-R^2}$ and $F(\lambda)$ is the Bessel transform of F(R). This can be interpreted as the "increase in temperature" due to the absorption of the laser beam, since one may also add a solution T=const which obeys the differential equation and the boundary conditions [8].

The general solution for the temperature shown in equation (9) can be rewritten in terms of a normalized temperature rise function N(R,Z,W) and the maximum temperature rise as:

$$\Delta T_{max}(R,Z,W) = \delta T_{max} N(R,Z,W) \tag{10}$$

Where the maximum temperature rise is according to Lax [8]

$$\delta T_{max} = \frac{P}{2\sqrt{\pi}\,Kw} \tag{11}$$

Here, the total incident power is P and we assume heating confined to the surface layer only (i.e., W→∞). The general expression of the function N(R,Z,W) has been shown to be per Lax [8]:

$$N(R, Z, W) = \frac{W}{\int_0^\infty F(\lambda)d\lambda} \int_0^\infty J_0(\lambda R) F(\lambda) \frac{W e^{-\lambda Z} - \lambda e^{-WZ}}{W^2 - \lambda^2} d\lambda \tag{12}$$

where $F(\lambda)$ is the Bessel transform of F(R).

In almost all practical cases, there is finite depth of penetration and it would be advantageous to know the temperature rise along the beam axis (i.e., R=0) and at the front surface (i.e., Z=0). So, the realistic temperature can be written on the beam axis and at the front surface to be the maximum temperature times the reduction factor N because of finite penetration depth as:

$$\Delta T_{max}(0,0,W) = \delta T_{max} N(0,0,W) \tag{13}$$

where $$N(0, 0, W) = \frac{1}{\sqrt{\pi}} \int_0^\infty e^{-\frac{\lambda^2}{4}} \left(\frac{W}{W+\lambda}\right) d\lambda \tag{14}$$

Equation (9) has been solved by Lax [8] in terms of Dawson and exponential integrals and the solutions for large (e.g., a metal sheet) and small values (gaseous sample like $SF_6$ cloud) of W (i.e., for highly absorbing and weakly absorbing targets) are $$N(0,0, W\to\infty)\to 1\,(\text{metal sheet}) \tag{15}$$

and $$N(0, 0, W\to 0) = \frac{W}{\sqrt{\pi}}\left(\ln\frac{2}{W} - \frac{\gamma}{2}\right)\,(\text{gas}) \tag{16}$$

where γ=0.5772 is Euler's constant.

Using equations (11), (13), (15) and (16), the steady state temperature rise in a metal sheet and in a $SF_6$ cloud at the front surface along the beam axis can be calculated.

Maximum temperature rise in strong absorber examples:

Copper (K=400 W/m-K), from equations (11) and (15): $\Delta T_{max}$=0.07° K; and Iron (K=80 W/m-K), from equations (11) and (15): $\Delta T_{max}$=0.353 K This sample calculation shows, dramatically, the role played by thermal conductivity in determining the temperature rise of the object. The lower the conductivity, higher will be the temperature rise. Thus, a gas cloud has the potential of exhibiting a higher temperature rise when the laser radiation is absorbed by the gas.

Maximum temperature rise in a weak absorber (gas cloud) examples:

The absorption coefficient of $SF_6$ peak at 10.55 μm wavelength can be extracted from PNNL data base [7]. PNNL data show a decadic absorbance of 0.04 $[ppm-m]^{-1}$ for $SF_6$ at 10.55 microns.

Absorption coefficient=α=ln(10)×absorbance $$\therefore \alpha = 0.092 \text{ (ppm.meter)}^{-1} \quad (17)$$

Gas density for 1 ppm at $STP = 2.68 \times 10^{13}$ $cm^{-3}$ $$\therefore SF_6 \text{ absorption cross section} = \sigma = 9.2 \times 10^{-4}/2.68 \times 10^{13} \quad (18)$$

$\sigma = 3.44 \times 10^{-17}$ $cm^{-2}$/molecule $$n_{SF_6}(1 \text{ ppm}) = 1 \text{ ppm } SF_6 \text{ density at } 300K \quad (19)$$
$$= 2.68 \times 10^{13} \times (273/300)$$
$$= 2.44 \times 10^{13} \text{ cm}^{-3}$$

So α (1 ppm, 300K)=σ×n=9.138×10$^{-4}$ $cm^{-1}$ and with 1 cm beam spot size we have W=α w=9.138×10$^{-4}$ (watts per cm). The thermal conductivity of air is K=0.026 W/m-K [9]. The actual maximum temperature rise (with respect to un-illuminated area) is calculated by using equations (11), (13) and (16) to be:

$$\Delta T_{max} \approx 4.1 \text{ K (1 ppm } SF_6, 1W \text{ } CO_2 \text{ laser at } 10.55 \text{ μm}, 1 \text{ cm radius beam}) \quad (20)$$

In the case of a gaseous absorber, it is instructive to parameterize the temperature rise with respect to two critical parameters: absorption coefficient of the gas and the spot size (radius) of the illuminating laser beam on the "cloud" containing the target molecule. Results of these calculations, using equations (11) and (16) and thermal conductivity of air to be 0.026 W/m-K, are shown in FIGS. 5 and 6 which emphasize different regions of interest.

Figure 5:
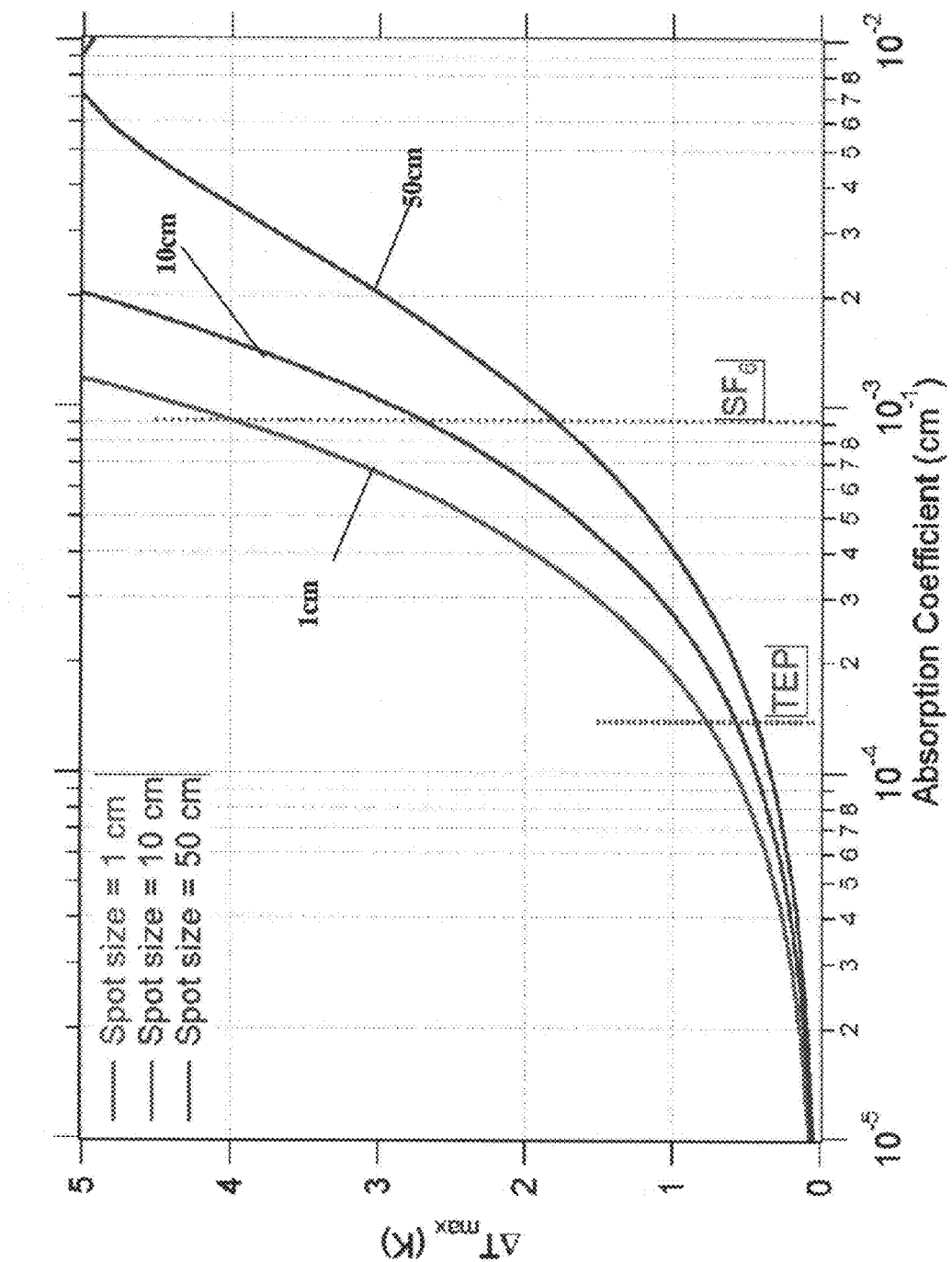
FIG. 5 graphically indicates a calculated temperature rise of the illuminated column of gas (containing the target molecule) as a function of the absorption coefficient emphasizing the region important for very strong absorbers such as $SF_6$ and TEP.

Shown in FIG. 5 is the calculated temperature rise of the illuminated column of gas (containing the target molecule) as a function of the absorption coefficient emphasizing the region important for very strong absorbers such as $SF_6$ and TEP. Results for using three different illumination spot sizes, 1 cm, 10 cm and 50 cm are shown. Positions of absorption coefficients for $SF_6$ and TEP are shown as vertical bars.

From FIG. 5, it can immediately be observed that $\Delta T_{max}$≈4.1 K, 2.7 K, and 1.8 K for spot sizes of 1 cm, 10 cms and 50 cms, respectively for $SF_6$. Similar information about TEP can also be read off from the figure.

Figure 6:
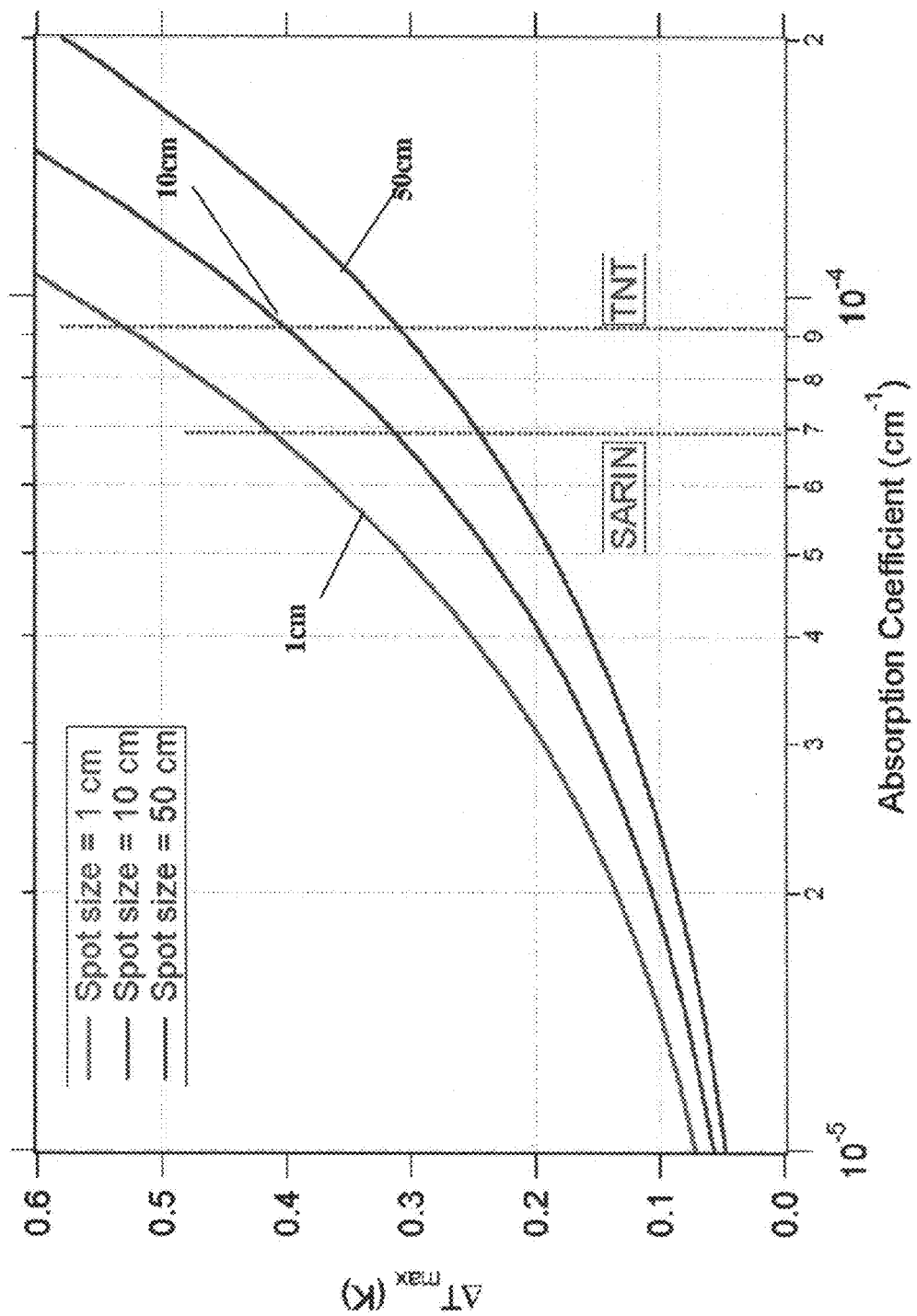
FIG. 6 is a calculated temperature rise of the illuminated column of gas (containing the target molecule) as a function of the absorption coefficient emphasizing the region important for strong absorbers such as TNT and Sarin.

From FIG. 6, it can be seen that for TNT at a temperature of ~122° F., $\Delta T_{max}$≈0.53 K, 0.4 K, and 0.32 K for illumination spot sizes of 1, 10 and 50 cms, respectively. Absorption coefficient for TNT has been derived from laser photoacoustic detection studies [11]. For 1 ppm of Sarin levels, significantly below human incapacitation, the expected $\Delta T_{max}$≈0.41 K, 0.32 K, and 0.24 K for illumination spot sizes of 1, 10 and 50 cms, respectively.

FIG. 6 shows the calculated temperature rise of the illuminated column of gas (containing the target molecule) as a function of the absorption coefficient emphasizing the region important for strong absorbers such as TNT and Sarin. Results for using three different illumination spot sizes, 1 cm, 10 cm and 50 cm are shown for target concentrations of 1 ppm, which for TNT corresponds to a temperature of ~50° C.

Time Dependent Behavior of Laser Induced Heating of a Gas Cloud

It can be seen that the heat produced (from temperature rise) in the $SF_6$ gas cloud due to laser absorption is small but finite. In such a system, convection can be neglected as a dissipation mechanism over short periods of time involved in lock-in detection of the radiated heat. This generally arises from the definition of convection as given by Lord Rayleigh which is as follows. "When heat is fed into the system from one direction, at small values it merely diffuses (conducts) from below upward, without causing fluid flow. As the heat flow is increased, above a critical value of the Rayleigh number, the system undergoes a bifurcation from the stable conducting state to the convecting state, where bulk motion of the fluid due to heat begins."

Gas is not a condensed medium, so thermal diffusion cannot be considered due to conduction (like in a metal) as a means of dissipation of heat from a gas. The only way the heated gas dissipates heat is through radiation. The emissivity of normal atmosphere (~79% $N_2$, 20% $O_2$, 350 ppb $CO_2$ and ~1% $H_2O$) is approximately 0.8 [10]. The largest contribution to the emissivity of air comes from $CO_2$ and $H_2O$. The concentration of $CO_2$ is relatively constant throughout the world and 1% water content is typical in most circumstances. However, the total emissivity is only a slowly varying function of the water content and varies from 0.6 for ~0.024% to 0.9 for 3% water (see FIG. 7).

Figure 7:
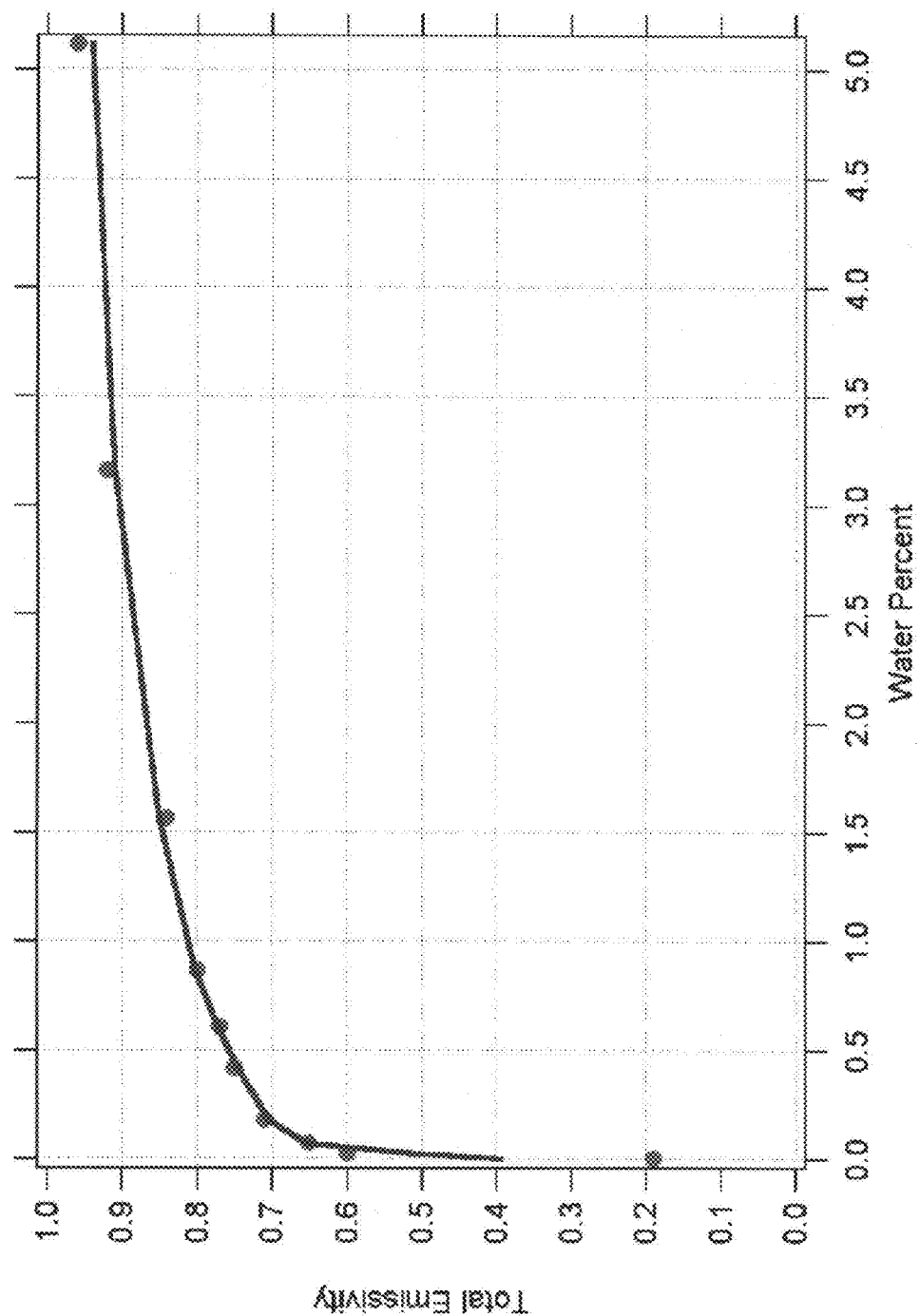
FIG. 7 shows atmospheric emissivity as a function of water content in percent.

FIG. 7 shows atmospheric emissivity as a function of water content in percent. $CO_2$ concentration is assumed to be constant at 350 ppb. Data are obtained from Staley and Jurica [10]. The solid line is shown to guide the eye.

Gagne and Chin [12] report experimental results of relaxation time of ~2 μs for $CO_2$ laser energy absorbed in dilute mixture of $SF_6$ gas in normal air. This means, if the $CO_2$ laser is chopped at 1 kHz, the heat produced in the gas will almost instantaneously follow the chopped excitation. This argument justifies the use of phase sensitive detection to enhance the sensitivity in this detection scheme. Furthermore, for a 1 cm diameter $CO_2$ laser beam interrogating the CWA/explosives vapor cloud, wind velocities of ≦30 km/h would not lead to appreciable degradation of the sensitivity of the system when using 1 kHz chopping rates.

Additionally, the relatively quick relaxation time enables a gas cloud to be interrogated very quickly with a significant, or even large, number of separate, identifying wavelengths. The resulting identifying thermal responses can be reliably gathered/detected in a short period of time. Some wavelengths may be repeated to confirm the thermal response of the gas cloud to the selected wavelength of laser light. Quick identification of harmful gasses may lead directly to fewer or may entirely prevent injuries and deaths.

Imaging of Blackbody Radiated Power on the Sensor

The sensor response can be calculated using the following procedure:

1. Calculate the total power radiated by the blackbody (in this case, the illuminated column of gas) from the "energy flux density" or "irradiance" which is power per unit area according to the Stefan-Boltzmann law. The temperature of the $SF_6$ cloud is just the measure of heat produced by the laser absorption, but physically what is radiated is the heat energy per unit volume per unit. time. It is assumed that the power is radiated isotropically in $4\pi$ steradians. For a CWA cloud that is small compared with the standoff distance, this is approximately true.

Figure 8:
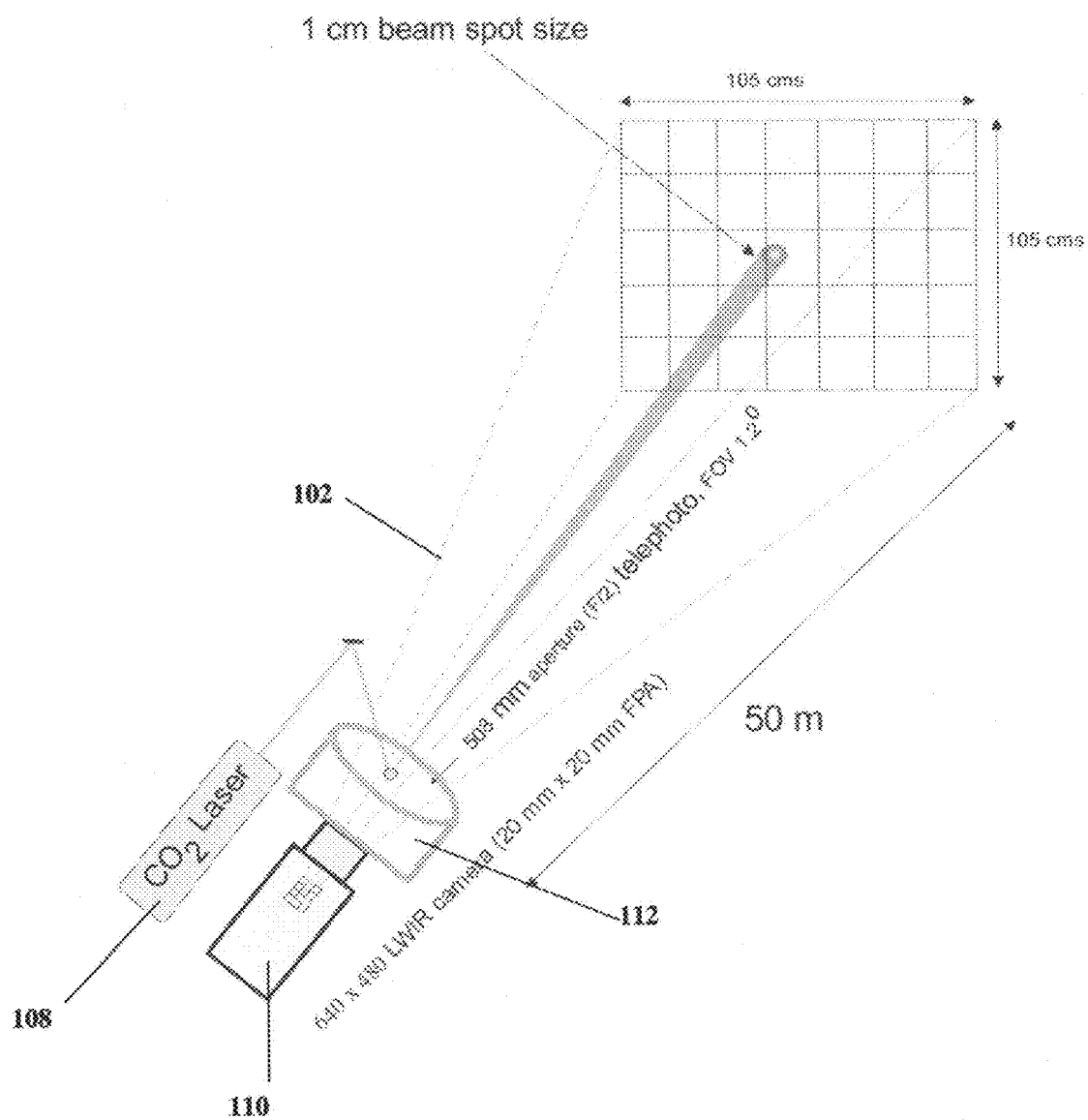
FIG. 8 shows the details of the ROSE standoff detection system.
Figure 9:
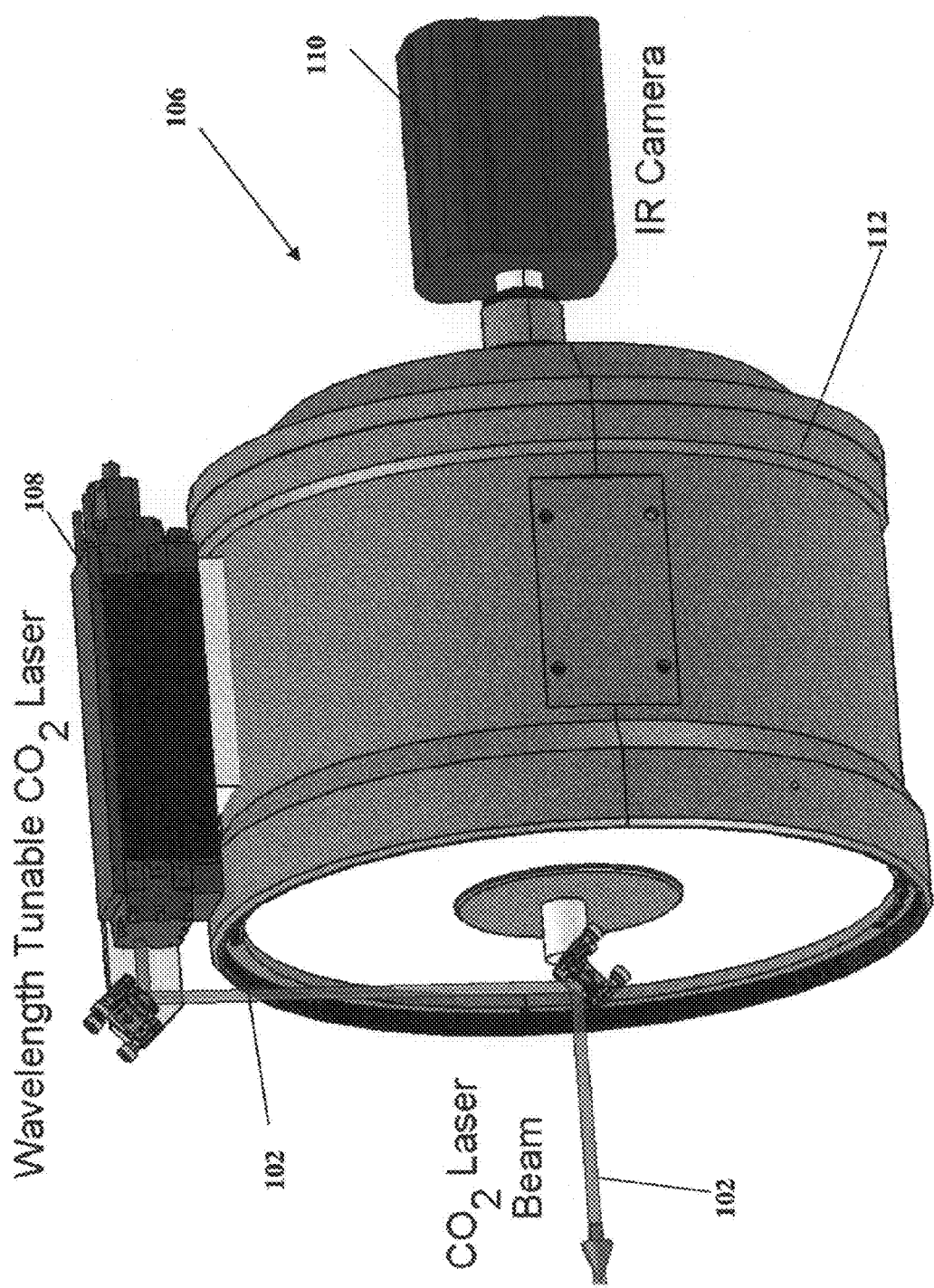
FIG. 9 is a conceptual drawing of the laser/telescope/infrared camera for ROSE detection of CWA/explosives vapors/TICS.

2. Calculate the fraction of the total blackbody radiated power from an elemental sphere of radius 1 cm (spot size) that is imaged onto the detector focal plane array (FPA). The imaged area on the FPA is important since that will be used to calculate the rise in temperature locally on the FPA. For maximal collection of the radiated blackbody power, look exactly in the direction of the laser beam, which is easy using an almost coaxial design of ROSE system (FIGS. 8 and 9). Find the contribution of power radiated by the entire column of gas along the viewing direction. This can be done by assuming the heated gas column to be made up of a line of elemental spherical radiators. The length of this full radiating element will be approximately $1/\alpha$. The power integrated over this entire length, along the viewing direction, z, of heated gas column will be imaged onto the FPA.

3. Calculate the rise in temperature knowing the fractional power being imaged onto the imaged area on the FPA. This will yield the detector response. The number of pixels illuminated by the imaged heated volume of the gas cloud will depend on the object area, the field of view (FOV) of the telescope, the distance, and the pixel density (pitch) of the FPA. The smaller the FOV of the telescope and the higher the pixel density (smaller pixel pitch) of the FPA, the higher the spatial resolution of viewing will be. Ideally, the 1 cm diameter column of the heated cloud is imaged on a single pixel of the camera to get the maximum contrast between the neighboring pixels. By knowing the detector response (detectivity) of one pixel (material and electronic readout) and the photon flux incident on it, the signal-to-noise ratio can be calculated accurately. This quantification of camera response becomes essential to estimate the correct PFA of the standoff detection system. The NETD in the industry refers to the noise equivalent temperature difference "on-the-scene" which is not a complete quantitative characterization of the optics-camera system like "detectivity" characterization of a detector.

A proposed schematic of a $CO_2$ laser irradiating a 1 cm$^2$ area of $SF_6$ cloud at a distance of 50 m from the sensor (source-camera) system is shown in FIG. 8.

FIG. 8 shows the details of a ROSE standoff detection system. The source-detector system is placed at a distance of ~50 meters from the target gas. For a pixel density 640×480, a viewing pixel of roughly 1 cm$^2$ will be imaged on a detector having pixel dimensions of 30 µm×30 µm (specification of a typical LWIR camera).

FIG. 9 shows a conceptual implementation of the Remote Optothermal Sensor (ROSE) system. For purposes of illustration and discussion, the telescope 112 for light collection is a compact 50 cm diameter f/2 catadioptric system (see Appendix 1 for the details of the telescopes). The wavelength tunable $CO_2$ laser 108 is mounted on the telescope chassis and the $CO_2$ laser beam 102 propagates collinearly and/or coaxially with the observing axis of the telescope 112. The ability to observe the excited cylindrical volume end on, as opposed to a small angle as shown in FIG. 2 for explanation of the principle is ideal for the present description since one can visualize the imaging of the entire column on a single pixel of the camera 110 mounted at the rear of the telescope.

Power Radiated by a Heated Column of Gas

The power density of radiation emitted by a blackbody is given by Stefan-Boltzmann law:

$$J = \epsilon \sigma T^4 \quad (21)$$

where $\epsilon$ is the emissivity, $\sigma$ is the Stefan-Boltzmann constant and T is the temperature of the blackbody in degrees Kelvin. The power density of heat radiated by the $SF_6$ cloud exposed to $CO_2$ laser radiation with respect to its surroundings (unexposed and/or no target gas) will be:

$$J = \varepsilon\sigma((T+\Delta T)^4 - T^4) \quad (22)$$
$$= \varepsilon\sigma((T^2 + 2T\Delta T + \Delta T^2)^2 - T^4)$$

Since $\Delta T$ is small compared to T, we approximate $(\Delta T)^2 \to 0$, So we have, $$J \approx \varepsilon\sigma((T^2 + 2T\Delta T)^2 - T^4) \quad (23)$$
$$\approx \varepsilon\sigma((T^4 + 4T^3\Delta T + 4T^2\Delta T^2) - T^4)$$

Again using $(\Delta T)^2 \to 0$ we have:

$$J \approx 4\epsilon\sigma T^3 \Delta T \quad (24)$$

The total power radiated spherically in $4\pi$ steradians will be $P = J \times A$, where A is the radiating area. Here the radiating area is taken as a cylinder of 1 cm diameter and a length of $\alpha^{-1}$ cm, where $\alpha$ is the absorption coefficient. For 1 ppm $SF_6$ at 10.55 microns, $\alpha \sim 0.001$ cm$^{-1}$, and the resulting length is approximately 10 meters.

Since the heated cylinder is viewed end-on, the total radiated power along the narrow cone angle subtended by the telescope FOV by the $1/\alpha$ length of the heated gas cloud needs to be calculated. Assuming a collimated laser beam, the radiating element will be a cylindrical rod of spot size radius and length $1/\alpha$. The heat radiated from the exposed cylindrical $SF_6$ gas column that reaches the IR camera will be contributed from its entire length. In order to use the spherically symmetric heat radiation model from a unit sphere of gas, the entire cylindrical gas column is broken up into a line of elemental spheres as shown in FIG. 10.

Figure 10:
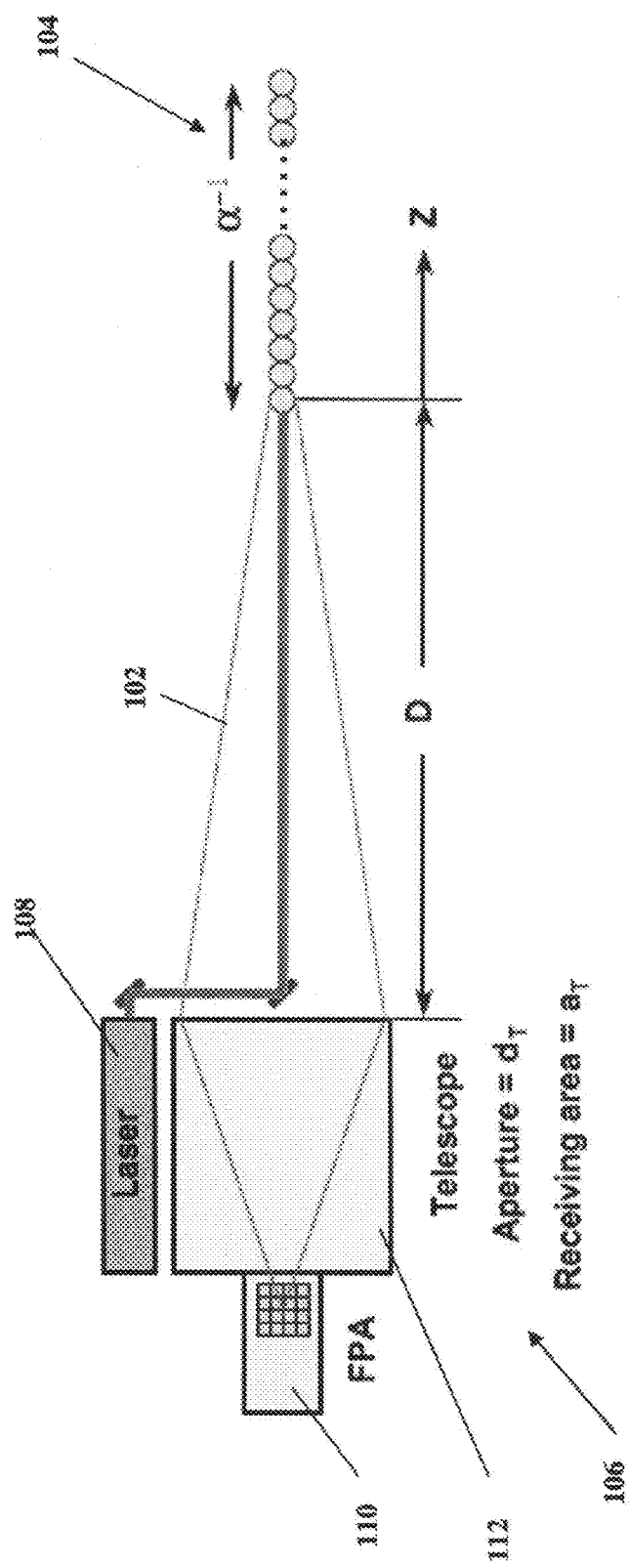
FIG. 10 is a model for calculating the heat received by the IR camera from a linearly distributed heat source (such as laser exposed $SF_6$ gas).

FIG. 10 shows a model for calculating the heat received by the IR camera from a linearly distributed heat source (laser exposed $SF_6$ gas).

The line of elemental spheres represents the heated gas column 104 of length $\alpha^{-1}$, the effective absorption length of the laser beam 102. The effective absorption length is basically the distance in which the beam intensity reduces by a factor of $\alpha^{-1}$ due to the absorption by the target gas. Each unit sphere of area A, as given above, radiates a spherically symmetric radiation pattern and contributes to the total thermal radiation received by the observation cone of the telescopic optics 112 of IR camera 110. As the laser beam 102 is attenuated on propagation, the temperature rise of each sphere however is not the same as calculated for the front surface (Z=0) in Equation (13) because the laser beam intensity diminishes as the beam propagates. So, to calculate the power contribution $J \times A$ from each sphere from Equation (24), $\Delta T$ for each sphere along the propagation of the laser beam 102 must be known. Ideally this solution exists in using Equation (12) in Equation (10). Here, we assume an exponential decay of ΔT vs. Z (Beer's law), is assumed, i.e., we are neglecting laser beam spreading over the 1/α distance. So it can be written $$\Delta T_{max}(0,Z,W) \approx \Delta T_{max}(0,0,W)e^{-\alpha Z} \quad (25)$$

where $\Delta T_{max}(0,0,W)$ has been estimated to be 4.1 K for 1 ppm $SF_6$ gas at 10.55 μm and Z is the propagation axis.

Considering the first unit sphere, the fractional power, $P_{F_r}$, received by the optics is:

$$P_{F_r} = \left(\frac{a_T}{4\pi D^2}\right)P \quad (26)$$

where $a_T$ is the aperture area of the receiving optics (receiving optics diameter $d_T$), D is the distance and P is the power radiated by the first unit sphere (FIG. 10).

Now $P = J \times A = 4\epsilon\sigma T^3 \Delta T \times A$ where $A = 4\pi \times 10^{-4}$ m² (surface area of the elemental radiation sphere) for a 1 cm diameter laser beam. The contribution from different spheres will come from two factors, namely the distance D and exp(−αZ) (Equation 25). Assuming a collimated laser beam and substituting all the factors in the above equation and considering the distance between consecutive spheres to be 2w (i.e., diameter of an elemental sphere) we have:

$$P_{F_r} = \frac{a_T}{4\pi} 4\epsilon\sigma T^3 \Delta T_{max}(0,0,W)A \times \sum_{i=1}^{\frac{1}{2w\alpha}} \frac{e^{-2w\alpha(i-1)}}{(D+2w(i-1))^2} \quad (27)$$

In the present case, w=1 cm, α~0.001 cm⁻¹ for 1 ppm $SF_6$ at 10.55 microns, and D=50 m (FIG. 3), we have:

$$P_{F_r} = \frac{a_T}{4\pi} 4\epsilon\sigma T^3 \Delta T_{max}(0,0,W)A \times \sum_{i=1}^{500} \frac{e^{-2\alpha(i-1)}}{(5000+2(i-1))^2} \quad (28)$$

Evaluating $$\sum_{i=1}^{500} \frac{e^{-2\alpha(i-1)}}{(5000+2(i-1))^2} = 1.455 \times 10^{-5}$$

and using σ=5.67×10⁻⁸ J s⁻¹ m⁻² K⁻⁴
T=300 K,
$\Delta T_{max}(0,0,W)$=4.1 K
ε√0.8

$$a_T = \frac{\pi}{4}(d_T)^2 = \frac{\pi}{4} \times (0.5)^2 m^2$$

we have:

$$P_{F_r} = 66 \, \mu W \quad (29)$$

The value of ε is obtained from Staley and Jurica [10] and FIG. 7.

This fractional power will be imaged onto the focal plane array of the IR camera. Also note that for only one elemental sphere (i=1) at the front (at Z=0), with a temperature rise of 4.1 K, we have $P_{F_r} \approx 0.18$ μW. The difference between the total received power in Equation (29) and this number comes from the contribution of all the elemental spheres considered in the summation above.

An object area 105 cm×105 cm (FIG. 8) is imaged onto an active area of 20 mm×20 mm (FPA), therefore the imaged area is reduced by a factor $2^2/105^2 = 3.63 \times 10^{-4}$. For a 30 μm×30 μm pixel pitch FPA (typical for MCT, mercury cadmium telluride) we can expect to image an object of 1 cm spot size at a 50 m distance to cover an area equal to 126 pixels on the camera.

Detection Sensitivity of ROSE

In this section, the signal-to-noise ratio for the detection of the "heated" column of gas is calculated when either an FPA camera or a single element detector is used.

ROSE Detection Sensitivity Using a Camera with an FPA and a Telescope

To be able to quantitatively characterize the operation of ROSE devices the way we have done in our L-PAS point sensors, camera performance must be carefully defined differently from "on-the-scene" NETD (noise equivalent temperature difference) as is customary in the industry. Although responsivity (volts per watt) is a performance measure of a particular IR detector, it is not useful as a standardized definition comparing different detector performance. On the other hand, interrelated definitions of NEP, D* & NETD involving signal-to-noise ratio offer useful figures-of-merit for comparing different FPAs.

The noise in a photon detector (not thermal) as in the present case (MCT FPA) is background fluctuation limited at cryogenic temperatures (Sterling cycle cooled FPA) and becomes generation-recombination limited as the temperature is raised. The NETD measuring the background fluctuation noise is a figure-of-merit for FPAs taking into account the optics, array and readout electronics, not including the display [13, 14, 15]. The background fluctuation noise, which limits the detector performance, essentially comes from the random fluctuation of temperature due to the heat exchange between the detector and its surroundings. Assuming only photon noise from radiating background (all other noise sources being negligible), NETD has been defined as [13, 14, 15]:

$$NETD = \frac{4F^2 \sqrt{B}}{\sqrt{A_{det}} \, \tau_0 D* \left(\frac{\Delta P}{\Delta T}\right)_{\lambda_1-\lambda_2}} \quad (30)$$

where $$F = \frac{f_T}{d_T}$$

is the f# of the telescope having a focal length $f_T$ and an aperture $d_T$, B is the sensor bandwidth, $A_{det}$ is the detector area, $\tau_0$ is the optical transmittance, $\Delta P/\Delta T$ is the thermal derivative of blackbody radiated power across the wavelength of interest $\lambda_1-\lambda_2$ and D* is the detectivity.

Knowing the NETD of the MCT FPA (Santa Barbara Focalplane: SYS640/512 MCT), to a catadioptric f/2 telescope (Stingray Optics: SR0322-A01), $\Delta P/\Delta T = 2.62 \times 10^{-4}$ W/cm² K for a 8-14 microns wavelength range [13], the value of D* from the above equation can be estimated. Using an NETD=20 mK, 1 Hz bandwidth, $\tau_0$=0.9 and a single pixel detector size ($A_{det}$) of 30 μm×30 μm shows:

$$D^* = 1.1 \times 10^9 \text{ cm Hz}^{1/2} \text{ W}^{-1} \tag{31}$$

This D* value of a single pixel detector of a sterling cycle cooled (66K) MCT FPA is 5.5 times higher than the 0.25 mm×0.25 mm single element room temperature MCT detectors ($D^*=2\times10^8$ cm Hz$^{1/2}$ W$^{-1}$ for model PVM-10.6 from Vigo Systems) presently being used. Also noteworthy is the fact that the above estimated D* of the presently available cooled MCT FPAs is still a few orders of magnitude lower than the theoretical performance limit of these devices [13].

To estimate an achievable "signal-to-noise" ratio in ROSE detection scheme, the definition of the noise equivalent power (NEP) as [15] is used:

$$NEP = \frac{\sqrt{A_{det} B}}{D^*} \tag{32}$$

In most practical cases however, the object (laser irradiated) will be focused onto a multi-pixel image area. To be able to estimate the "signal-to-noise" ratio achievable in any image area, a generalized expression for the NEP is derived. This is done by substituting D* in the expression of NEP given above. Combining equations (30) and (32) a generalized relationship between NEP and NETD is obtained:

$$NEP = \frac{A_{det}\, NETD\, \tau_0}{4F^2}\left(\frac{\Delta P}{\Delta T}\right) \tag{33}$$

For a 1 Hz bandwidth and a 30 μm square single pixel detector, we have an NEP~$2.7\times10^{-12}$ W per pixel.

In the above example, the 1 cm spot size (beam waist) at 50 meters is imaged roughly to a detector area $3.14\times3.63\times10^{-4}$ cm$^2$=$11.4\times10^{-4}$ cm$^2$. This area corresponds to ~126 pixels. Thus, the power incident on each pixel is:

$$P_{pixel} \approx 66/126 \approx 0.52 \text{ μW} \tag{34}$$

which is just the fractional power, $P_{Fr}$, per equation (29) divided by the number of pixels receiving that power.

Thus the thermal radiation of 0.52 μW imaged onto a pixel gives a signal-to-noise ratio of:

$$SNR \approx \frac{0.52 \times 10^{-6}}{2.7 \times 10^{-12}} \approx 1.94 \times 10^5 \tag{35}$$

ROSE Detection Sensitivity using a Single Element Detector and a Telescope

Better signal detection capability may be attained by using a properly optimized single element MCT (mercury cadmium telluride) detector. A commercially available TE-cooled MCT detector (e.g., PVI-3TE-10.6 from Vigo Systems) that exhibits $D^*=2.5\times10^9$ cm Hz$^{1/2}$ W$^{-1}$ is considered. In selecting a detector with a sensitive area of 0.5 mm×0.5 mm, a NEP (noise equivalent power or the smallest detectable power) of $\sim2\times10^{-11}$ W is used. In the above example, the 1 cm spot size at 50 meters is imaged into an area of ~$11.4\times10^{-4}$ cm$^2$, which is smaller than the 0.5 mm×0.5 mm size MCT detector (area of $25\times10^{-4}$ cm$^2$). Thus, all of the thermal radiation of 66 μW is imaged on the detector, giving a signal-to-noise ratio (in 1 Hz bandwidth) of $$\frac{S}{N} \approx \frac{66 \times 10^{-6}}{2 \times 10^{-11}} \approx 3.3 \times 10^6 \tag{36}$$

The signal-noise-ratio obtained using a single element commercial grade TE-cooled MCT detector is considerably larger than that obtained with a standard FPA camera because of the small pixel size in the camera under consideration, which leads to the spread of the imaged area over many (~126) pixels. Performance with specialized FPA cameras specifically sized for the ROSE application could clearly reach the capability of single element commercial sensor.

Implication of the SNR Calculated for FPA Camera and a Single Element Detector

In either case, the detection of thermal radiation from the laser power absorbed in the gas cloud is eminently feasible. The distance dependence of detectability is proportional to $D^{-2}$. Thus, with the SNR of >100,000 in either of the cases we can easily increase the standoff distance to 1 km and retain a SNR of >300, through the use of appropriate telescope for light/heat collection.

Proof-of-Concept for the Detection of TNT at 0.5 Km

Having derived general expressions for the standoff detection of a cloud containing the target gas, we can now look at a specific case of detection of a TNT plume from a distance. Unlike the release of a target gas such as CWAs for which the analysis of the feasibility calculation of Section VI (above) is applicable, for the standoff detection of explosives, the very localized nature of the vapors release needs to be taken into account. This will limit the size of the "cloud" that is needed for interrogation/evaluation. In the analysis below, the "cloud" will be truncated to 10 meters (rather than the $\alpha^{-1}$ distance assumed for a CWA release in the atmosphere).

Again, for proof-of-concept calculations and demonstration of standoff detection of TNT at 500 meters, SF$_6$ will be used as a surrogate because it is relatively benign and early experiments can be done without having to go to appropriate federal facilities where needed quantities of TNT samples can be located at 500 meter distances. By choosing appropriate vapor pressure of SF$_6$ the infrared absorption caused by 1 ppm of TNT will be duplicated.

SNR Calculations (FPA Camera with 640×480 Pixels)

The SNR per pixel is given by:

S/N=Power incident on FPA per pixel/NEP per pixel

The "power incident on FPA per pixel" is calculated from the fractional power given by Equation 27 as:

$$P_{F_r} = \frac{\alpha_T}{4\pi} 4\varepsilon\sigma T^3 \Delta T_{max}(0, 0, W) A \times \sum_{i=1}^{\frac{1}{2w\alpha}} \frac{e^{-2w\alpha(i-1)}}{(D + 2w(i-1))^2} \tag{27}$$

The received power is reduced appropriately (according to telescope FOV) from the object to the imaged area on the FPA. Knowing the area of a single pixel, the "power incident on FPA per pixel" is equal to $P_{F_r}/\eta$, where "$\eta$" is the total number of pixels in the imaged area. The factor "$\eta$" can be written as:

$$\eta = \left(\frac{A_{FPA}}{A_{obj}}\right) \times \left(\frac{\pi w^2}{A_{det}}\right) \tag{37}$$

where, $A_{FPA}$ is the FPA active area, $A_{obj}$ is the target area, $A_{det}$ is the detector area (pixel) and w is the laser spot size.

Using the aperture of telescope $$a_T = \left(\frac{\pi}{4}\right)d_T^2$$

and the total surface area of radiating spheres $A=4\pi w^2$, we have:

$$\frac{P_{F_r}}{\eta} = d_T^2 \varepsilon \sigma T^3 A_{det} \Delta T_{max}(0, 0, W) \left(\frac{A_{obj}}{A_{FPA}}\right) \sum_{i=1}^{\frac{1}{2w\alpha}} \frac{e^{-2w\alpha(i-1)}}{(D+2w(i-1))^2} \quad (38)$$

where the summation is over the appropriate plume depth, taken here as $\alpha^{-1}$.

The generalized expression for NEP is given by Equation 33 as:

$$NEP = \frac{A_{det} NETD\tau_0}{4F^2}\left(\frac{\Delta P}{\Delta T}\right) \quad (33)$$

Combining Equations (27) and (33), a generalized expression is derived for the SNR per pixel of the FPA, $$SNR = \frac{4 f_T^2 \varepsilon \sigma T^3 \Delta T_{max}}{NETD\tau_0\left(\frac{\Delta P}{\Delta T}\right)} \left(\frac{A_{obj}}{A_{FPA}}\right) \sum_{i=1}^{\frac{1}{2w\alpha}} \frac{e^{-2w\alpha(i-1)}}{(D+2w(i-1))^2} \quad (39)$$

Inserting in this expression, the experimental factors including the calculated maximum temperature rise $\Delta T_{max}$, spot size of laser beam w, distance D, absorption coefficient $\alpha$, the telescope focal length $f_T$, camera parameters NETD and $A_{FPA}$, emissivity $\varepsilon$ of the atmosphere and $\Delta P/\Delta T$ for the blackbody radiation, the SNR for a particular scenario can be estimated. The summation above is made for $\alpha^{-1}$ distance. However, for finite size plumes, such as those emanating from localized explosives, the upper limit will be truncated for appropriate "plume" depth.

The SNR for a "10 meter size plume of 1 ppm TNT" surrogate at a distance of 500 m for different spot sizes is calculated below. The parameters needed in the SNR calculation are:

Focal length of lens f=101.6 cms (f/2.0 detection telescope)
Emissivity $\varepsilon$=0.8
Stefan-Boltzmann constant $\sigma$=5.67×10$^{-8}$ J s$^{-1}$ m$^{-1}$ K$^{-4}$
T=300 K
$A_{obj}$=9×10$^5$ cm$^2$ for 1.2° full diagonal angle FOV and 508 mm aperture telescope
$A_{FPA}$=4 cm$^2$, for 20 mm×20 mm FPA (640×480 pixels)=9×10$^{-5}$ cm$^{-1}$
NETD=20 mK
$\tau_0$=0.9

- $\left(\frac{\Delta P}{\Delta T}\right) = 2.62 \times 10^{-4} Wcm^{-2}K^{-1}$

D=500 m

Putting these parameters in the above expression we have:

$$SNR = 25.3 \times 10^{10} \Delta T_{max} \sum_{i=1}^{n} \frac{e^{-2w\alpha(i-1)}}{(D+2w(i-1))^2} \quad (40)$$

For a plume size of 10 m, the SNR for different laser spot sizes can be calculated and the results are given in Table 2 below. Note that for a finite plume size (10 meters) the summation will be truncated for different n for different spot size diameters in order to remain within the 10 meter size of the plume.

TABLE 2

Calculated values of SNR for detection of a 1 ppm TNT plume of 10 meter dimension located at a distance of 0.5 km from ROSE. Calculations are for a 1.01 m F/2 telescope and a FPA camera with a 2 cm × 2 cm MCT array (640 × 480 pixels)

| Laser Spot Size | $\Delta T_{max}$ | Truncation | Truncation Factor | SNR |
|---|---|---|---|---|
| 2 cm | 0.52 K | n = 250 | 9.38 × 10$^{-8}$ | 1.2 × 10$^4$ |
| 4 cm | 0.46 K | n = 125 | 2.78 × 10$^{-8}$ | 3.2 × 10$^3$ |
| 10 cm | 0.4 K | n = 50 | 1.88 × 10$^{-8}$ | 1.9 × 10$^3$ |
| 25 cm | 0.36 K | n = 20 | 7.5 × 10$^{-7}$ | 680 |

SNR Calculations (Single Element Detector)

In Section VI above, regarding imaging of blackbody radiated power on the sensor, it was shown, that matching the pixel size to the imaged laser beam size is the optimum detection strategy. We explore below the improvement in the SNR over the previous case where we have used an FPA camera as the detector. The imaged area on the detector at the telescope focal plane is $$a_{image} = \pi w^2 \times \left(\frac{A_{FPA}}{A_{obj}}\right) \quad (41)$$

For an optimum detection strategy, the detector active area to the imaged area in Equation (41) needs to be matched. The relevant NEP can then be calculated from the D* for the MCT detector.

Substituting $$A = 4\pi w^2 \text{ and } a_T = \left(\frac{\pi}{4}\right)d_T^2$$

in Equation (27), we have $$P_{F_r} = \pi w^2 d_T^2 \varepsilon \sigma T^3 \Delta T_{max}(0, 0, W) \sum_{i=1}^{n} \frac{e^{-2w\alpha(i-1)}}{(D+2w(i-1))^2} \quad (27a)$$

This fractional power divided by the estimated NEP of a single element detector gives the SNR in the case of single MCT detector sized to match the imaged area. Note that the NEP will change as the detector size is changed to match the imaged area, D* remaining constant. Table 3, below, gives SNR estimates for the same parameters that were used for SNR calculations for a FPA detector shown in Table 2.

TABLE 3

Calculated values of SNR for detection of a 1 ppm TNT plume of 10 meter dimension located at a distance of 0.5 km from ROSE. Calculations are for a 1.01 m F/2 telescope and a single element detector (Vigo Systems model PVI-3TE-10.6 having a D* = 2.5 × 108 cm Hz$^{1/2}$W$^{-1}$) sized to match the imaged area of the laser spot size on the target plume.

| Laser Spot Size (cm) | $P_{Fr}$ (W) | Image Size (cm$^2$) | NEP (W) | SNR |
|---|---|---|---|---|
| 2 | 18.4 × 10$^{-8}$ | 5.6 × 10$^{-5}$ | 3 × 10$^{-12}$ | 6 × 10$^4$ |
| 4 | 20.0 × 10$^{-8}$ | 2.24 × 10$^{-4}$ | 6 × 10$^{-12}$ | 3.3 × 10$^4$ |
| 10 | 7.36 × 10$^{-7}$ | 1.4 × 10$^{-3}$ | 15 × 10$^{-12}$ | 4.9 × 10$^4$ |
| 25 | 1.64 × 10$^{-6}$ | 8.75 × 10$^{-3}$ | 37 × 10$^{-12}$ | 4.4 × 10$^4$ |

As anticipated, use of an optimized single element detector provides improved SNR for ROSE detection of explosives. On the other hand, an FPA detector provides a spatial image, which would be of value. Thus, for an eventual deployment of the ROSE detectors, specially fabricated FPAs will be desirable.

Proof-of-Concept Experiment

As mentioned above, the feasibility of standoff detection of TNT by using $SF_6$ as the surrogate and use of the $SF_6$ concentration that replicates the infrared absorption caused by 1 ppm of TNT vapor is demonstrated analytically. From measurements of a TNT absorption carried out using L-PAS techniques [11] and from PNNL data base for $SF_6$ infrared absorption, it is seen that ~100 ppb of $SF_6$ exhibits approximately the same infrared absorption as does 1 ppm of TNT vapor.

If a laser beam is focused to a spot size of w by a lens/mirror of appropriate focal length. The detection of a "TNT plume" surrogate at a distance of D will be carried out using an appropriate telescope for focusing the laser radiation into a spot size w. The required final laser lens/mirror diameter, d, can be calculated using the expression $$d = \frac{2\lambda f}{\pi w} \quad (42)$$

where the f is the focal length of the final lens/mirror for focusing the interrogating laser radiation. The confocal parameter i.e., the Rayleigh range (distance over which the focused laser spot size changes by a factor of $\sqrt{2}$), is given by $$w = 2 \text{ cms } 2z_0 = \frac{2\pi w^2}{\lambda} \quad (43)$$

For, w=2 cm, it is found that the final focusing lens diameter (for the proof-of-concept demonstration) to be d=15 cms. The confocal parameter (Rayleigh range) for this case is 2 $z_0$=237 meters. This is very long compared to the plume dimension and therefore the laser beam spot size is considered as constant over the 10 meter plume dimension.

Figure 11:
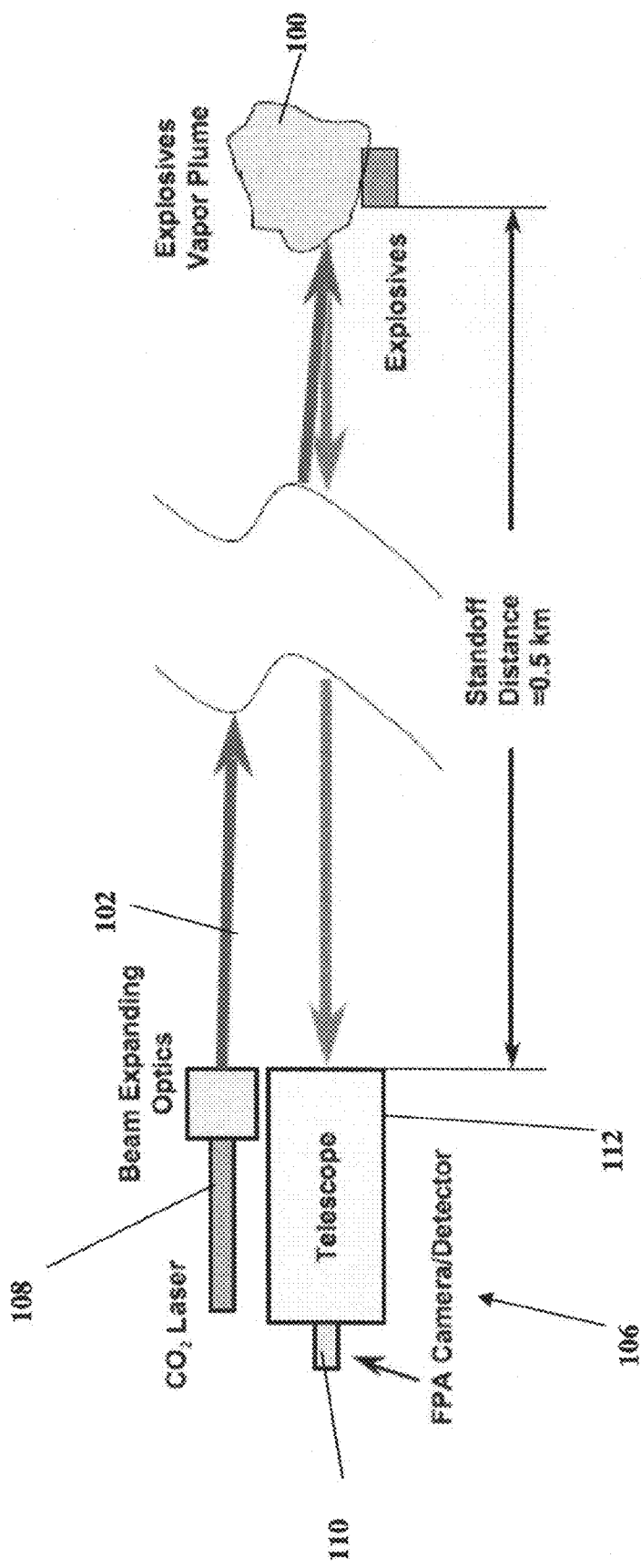
FIG. 11 is a schematic of the ROSE system for standoff detection at 0.5 km with beam expansion optics for the laser to create a 2 cm illuminated spot at the target.

FIG. 11 is a schematic of ROSE for standoff detection at 0.5 km with beam expansion optics for the laser 108 to create a 2 cm illuminated spot at the target 100.

The final laser focusing lens/mirror diameter required for generating a 2 cm spot size at 500 meters is only 15 cms. The experimental geometry is shown in FIG. 11. Although desirable, it is not be possible to have collinear propagation of the laser beam 102. However, to the offset between the laser axis and the detection telescope axis may be ~33 cm which introduces negligible correction for end-on observation of the illuminated column of gas. Thus, from the above estimates, it is seen that the "1 ppm TNT" surrogate 10 m plume at a distance of 500 m can be detected using our proposed ROSE sensor with an SNR of >10$^4$ using a FPA camera 110 with a 2 cm×2 cm FPA having 640×480 pixels.

Distance Dependence of the Performance of ROSE

As a first order approximation, the excess blackbody radiation from the "heated" target gas volume received by the optical telescope varies as 1/D$^2$. Thus the SNR will vary approximately as 1/D$^2$. However, a proper choice in the telescope and the FPA camera (or a single element detector) that permits all the collected radiation from the heated column of the target gas to be imaged on to a single pixel would make the distance dependence somewhat slower than the 1/D$^2$. It is estimated that acceptable SNR (i.e., >100) can be achieved at standoff distances as great as 2 km. Considerable more analysis is necessary to get the exact distance dependence.

Response Times of IR Camera—Phase Sensitive Detection

Appendix 2 provides data for some of the commercially available infrared imaging detectors (cameras). From this, it is noted that QWIP (quantum well infrared photodetector) devices limit chopping speeds to several hundred fps while MCT devices can typically run at 1600 fps. An MCT FPA LWIR camera apparently is the best choice in considering the fast response times and allowing lock-in detection at 1 kHz for improving the signal-to-noise ratio estimated in earlier sections.

CONCLUSION

The feasibility of standoff detection of explosives, CWAs and TICs has been shown by analysis above. The problem is extremely challenging and a substantial amount of additional analytical work may be necessary to arrive at an optimum solution for standoff detection at distances of up to more than a kilometer, which is apparently quite possible. While the present proposal uses a 1 W $CO_2$ laser as the active source for demonstration and verification of the principle of ROSE, higher power $CO_2$ lasers or high power tunable QCLs may be used in the full-fledged implementation of the ROSE program.

While the present invention has been described with regards to particular embodiments, it is recognized that additional variations of the present invention may be devised without departing from the inventive concept. For example, if specific radiation wavelengths from target gas molecules arise from predictable and reliable molecular transitions, it may be possible to use a plurality of distinct wavelengths for target illumination if such identifying radiation can be detected from the target gas molecules. This may further reduce the time necessary to resolve the constituents of the target gas. Also, additional optical techniques may be used to transmit the laser beam and/or gather the resulting thermal radiation from the target gas. Such techniques may allow target gas detection and identification from greater distances.

Additionally, other chemicals may be detected by the system and method set forth herein including the vapors and precursors for making homemade explosives. These will often include, among other chemicals, acetone, hexamethylenetetramine/hexamine, hydrogen peroxide, and combinations thereof. These precursor constituents can be used for making homemade explosives such as TATP and HMTD.

Additionally, vapors from explosives like PETN, RDX, HMTD, ammonium nitrate, urea nitrate, nitroglycerin, combinations thereof and otherwise may also be advantageously pursued and possibly detected by the present invention.

Furthermore, in order to provide detection for a variety of light-reactive substances, wavelength regimes of 3.5 µm to 12 µm, 0.35 µm to 4 µm, 4.8 µm to 7.5 µm, 2.4 µm to 3.0 µm, and 3.4 µm to 4.0 µm may be utilized. Corresponding light sources for these wavelength regimes include respectively quantum cascade lasers, interband recombination diode lasers, $^{12}CO$ and $^{13}CO_3$, HF (hydrogen fluoride) lasers, and DF (deuterium fluoride) lasers. By exploiting optical characteristics of susceptible gases, and by irradiating these susceptible substances by a sufficient number of wavelengths, constituents of unknown conglomerations of chemicals may be advantageously detected.

Furthermore, in providing a source of illumination for the present invention, sources of incoherent illumination may be used and may include a blackbody light source of sufficient power to elicit sufficient response from the cloud or suspect/target gas/substance to be interrogated optically. In using a powerful blackbody source of optical power generating a sufficient amount of light (in the pertinent or appropriate spectrum regime), a number of filters and/or selection/detection devices may be used. Such devices include a narrow band pass filter for the wavelength regime of interest such that the blackbody radiation is selectively chosen so that only a selected wavelength at a time is transmitted. Additionally, a grating spectrometer may also serve a similar purpose as may as a Fourier transform spectrometer. A Fourier transform spectrometer may be able to provide transmission and/or analysis of a plurality of simultaneous wavelengths in the region of interest. For the Fourier transform spectrometer, radiation detected from the gas that occurs as a result of the intentional irradiation thereof may be analyzed by transforming the detected thermal signals to the appropriate wavelength domain.

APPENDIX 1

Commercially Available Compact Telescopes

TABLE 1

LWIR telescope Selection

| Supplier | Telescope Type | Aperture (mm) | Focal Length (cm) | FOV (°) |
|---|---|---|---|---|
| Stingray Optics | Catadioptric Model: SR0322-A01 | 508 | 101 | 1.2 |
| Jenoptics-IR | Lenses | 130 | 130 | 6.15 |
| DRS-infrared | Lenses | 103 | 103 | 7.9 |
| FUR Systems | Lenses | 76 | 76 | 10.55 |

In the model calculations in the proposal, we have used the Stingray Optics 508 mm telephoto optics (FOV~1.2°) in combination with 640×480 MCT FPA cameras (see Appendix 2).

APPENDIX 2

Commercially Available Infrared Imaging Systems

TABLE 2

LWIR Focal Plane Arrays

| Company | FPA Type | Frames per second (fps) | Pixel Density | NETD (mK) | Spectral Response (µm) |
|---|---|---|---|---|---|
| Jenoptic | Microbolometer | 60 | 640 × 480 | 90 | 7.5-14 |
| FLIR Systems | Microbolometer QWIPs | 60 | 640 × 480 640 × 512 | 90 35 | 7.5-13.5 8-9.2 |
| DRS IR | Microbolometer | 60 | 640 × 480 | 90 | 7.5-14 |
| SBFPMCT | >1K (Model: SYS640/512 MCT) | 640 × 480 | 20 | 8-12 | |
| SEIR | QWIPs MCT | >1K >1K | >1K 1K × 1K | 25 18 | 10-15% of peak 8-12 |

Comparison of the Above FPAs:

Microbolometers are broad band but slow (low fps) with relatively high NETD

QWIPs are small bandwidth devices. Low quantum efficiency (~10%) and so requires more integration time (~2 ms per pixel), typically run below 200 fps. Relatively low NETD.

MCTs are broadband, very high efficiency requiring fast integration times (~100 µs), can be run at 1600 fps/frames per second (a window of 256×256 pixels can be run at 1000 fps), very low NETD.

QWIPs and MCTs are good choices in our case since microbolometers have relatively high NETD and are slow. MCT FPA is the better choice in our case considering their broadband operation, lock-in detection possibility (very fast fps) and lowest NETD (15-20 mK).

Lockheed-Martin Santa Barbara Focal Plane (www.sbfp.com) and SE-IR corporation (www.seir.com), both in Santa Barbara, integrate customer provided FPAs (QWIPs and MCTs) and optics with closed cycle Sterling cycle coolers and provides the drive electronics and software to make the final LWIR camera.

REFERENCES

[1] See for example, Department of the Army. *Army Field Manual No. 3-9; Potential Military Chemical/Biological Agents and Compounds*, pp. 19-20. (Headquarters of the Army, Washington, D.C., Dec. 12, 1990); B. McNamara and L. Leitnaker, "Toxicological Basis for Controlling Emission of GB into the Environment", *Edgewood Arsenal Special Publication* (U.S. Army, Medical Research Laboratories, Edgewood Arsenal, Aberdeen Proving Grounds, Maryland. March 1971); Department of Health and Human Services, Center for Disease Control, "Final Recommendations for Protecting the Health and Safety Against Potential Adverse Effects of Long-Term Exposure to Low Doses of Agents: GA, GB, VX, Mustard Agent (H, HD and T) and Lewisite (L), *Federal Register* 53, 8504-8507 (Mar. 15, 1988).

[2] The first noticeable health effect is miosis, which for Sarin includes pinpointing of the pupil of the eye accompanied by runny nose, tightness of the chest and eye pain.

[3] Jimmie C. Oxley, James L. Smith, Kajal Shinde and Jesse Moran, "Determination of the Vapor Density of Triacetone Triperoxide (TATP) Using a Gas Chromatography Head Space Technique" *Propellants, Explosives, Pyrotechnics* 30, 127-130 (2005) and references cited therein.

[4] Ilya Dunayevskiy, Alexei Tsekoun, Manu Prasanna, Rowel Go and C. Kumar N. Patel "High Sensitivity Detection of Triacetone Triperoxide (TATP) and Its Precursor Acetone," *Applied Optics* 46, 6397-6404 (2007).

[5] M. E. Webber, M. B. Pushkarsky and C. K. N. Patel, "Optical detection of chemical warfare agents and toxic industrial chemicals: Simulation," J. Appl. Phys. 97, 113101 (2005).

[6] M. B. Pushkarsky, M. E. Webber, T. Macdonald and C. K. N. Patel, "High sensitivity, high selectivity detection of chemical warfare agents." Appl. Phys. Lett. 88, 044103 (2006).

[7] S. W. Sharpe, R. L. Sams, T. J. Johnson, P. M. Chu, G. C. Rhoderick and F. R. Guenther, SPIE proceedings for Vibrational Spectroscopy-based Sensor Systems 4577, 12-24 (2001).

[8] M. Lax, "Temperature rise induced by a laser beam," J. Appl. Phys. 48, 3919-3924 (1977).

[9] CRC Handbook of chemistry & physics, 81st Edition, 2000-2001, p 12-196, David R. Lide Ed-in-Chief, CRC Press.

[10] D. O. Staley and G. M. Jurica, "Effective Atmospheric Emissivity under Clear Skies," J. Appl Meteorology 11, 249-356 (1972).

[11] Michael Pushkarsky, Ilya Dunayevskiy, Manu Prasanna, Alexei Tsekoun, Rowel Go and C. Kumar N. Patel, "Sensitive Detection of TNT," Proc. Nat. Acad. Sciences 103, 19630-19634 (2006).

[12] M.-C. Gagne and S. L. Chin, "Energy relaxation time in a gas mixture measured by a photothermal probe beam deflection technique," Appl. Phys. B 52, 352-358 (1991).

[13] P. W. Kruse, "A comparison of the limits to the performance of thermal and photon detector imaging arrays," Infrared Phys. & Technol., 36, 869-882 (1995).

[14] P. G. Datskos, N. V. Lavrik and S. Rajic, "Performance of uncooled microcantilever thermal detectors," Review of Scientific Instruments, 75, 1134-1148 (2004).

[15] F. J. Crawford, "Electro-Optical Sensors Overview," IEEE AES Systems Magazine, 17-24, (October, 1998).

What is claimed is:

1. A system for the remote detection of gasses in a gas cloud, comprising:
a laser system tuned to a first wavelength of interest for a first gas, said laser system adapted for illuminating from a distance the gas cloud, said laser system including a tunable laser system tunable to a plurality of wavelengths characteristic of absorption wavelengths of said first gas in a range of approximately 9 µm to 11.5 µm;
said laser system tunable to a sufficient plurality of wavelengths to discriminate target gasses against interferents, said laser system illuminating the gas cloud with said plurality of wavelengths and with separate illuminations for each wavelength;
a heat sensor adapted for detecting heat generated by the gas cloud when the gas cloud absorbs said first wavelength such that said first gas is at least partially detectable in the gas cloud by illuminating the gas cloud with said first wavelength and by detecting heat generated by at least said first gas with said heat sensor, said heat sensor capable of sensing transient molecular relaxation of a laser-stimulated portion of the gas cloud, said transient molecular relaxation occurring on the order of microseconds, said heat sensor capable of sensing a higher temperature in a portion of the gas cloud illuminated by said laser; and
said heat sensor capable of sensing transient molecular relaxation of a laser-stimulated portion of a gas cloud for each of said separate illuminations, said separate illuminations selected from the group consisting of illuminations separated by intervals of time, illuminations sequentially transmitted in a continuous manner, and combinations thereof.

2. A system for the remote detection of gasses in a gas cloud as set forth in claim 1, wherein said laser system further comprises:
a $^{12}CO_2$ laser and $^{13}CO_2$ laser.

3. A system for the remote detection of gasses, comprising:
a laser tuned to a first wavelength of interest for a first gas, said laser adapted for illuminating from a distance a cloud of gas; and
a heat sensor adapted for detecting heat generated by a gas absorbing said first wavelength; whereby
said first gas is detectable in a gas cloud by illuminating said gas cloud with said first wavelength and by detecting heat generated by said first gas with said heat sensor.

4. A system for the remote detection of gasses as set forth in claim 3, further comprising:
said laser including a tunable laser tunable to a plurality of wavelengths.

5. A system for the remote detection of gasses as set forth in claim 4, wherein said tunable laser further comprises:
a tunable laser tunable to wavelengths characteristic of absorption wavelengths of said first gas.

6. A system for the remote detection of gasses as set forth in claim 5, wherein said tunable laser further comprises:
said tunable laser tunable to wavelengths in a range of approximately 9 µm to 11.5 µm.

7. A system for the remote detection of gasses as set forth in claim 6, wherein said tunable laser further comprises:
a $^{12}CO_2$ laser and $^{13}CO_2$ laser.

8. A system for the remote detection of gasses as set forth in claim 5, wherein said tunable laser further comprises:
said tunable laser tunable to wavelengths in a range of approximately 3.5 µm to 12 µm.

9. A system for the remote detection of gasses as set forth in claim 8, wherein said tunable laser further comprises:
a quantum cascade laser.

10. A system for the remote detection of gasses as set forth in claim 5, wherein said tunable laser further comprises:
said tunable laser tunable to wavelengths in a range of approximately 0.35 µm to 4 µm.

11. A system for the remote detection of gasses as set forth in claim 10, wherein said tunable laser further comprises:
a interband recombination diode laser.

12. A system for the remote detection of gasses as set forth in claim 5, wherein said tunable laser further comprises:
said tunable laser tunable to wavelengths in a range of approximately 4.8 µm to 7.5 µm.

13. A system for the remote detection of gasses as set forth in claim 12, wherein said tunable laser further comprises:
a $^{12}CO$ and a $^{13}CO$ laser.

14. A system for the remote detection of gasses as set forth in claim 5, wherein said tunable laser further comprises:
said tunable laser tunable to wavelengths in a range of approximately 2.4 µm to 3.0 µm.

15. A system for the remote detection of gasses as set forth in claim 14, wherein said tunable laser further comprises:
a HF laser.

16. A system for the remote detection of gasses as set forth in claim 5, wherein said tunable laser further comprises:
said tunable laser tunable to wavelengths in a range of approximately 3.4 µm to 4.0 µm.

17. A system for the remote detection of gasses as set forth in claim 16, wherein said tunable laser further comprises:
a DF laser.

18. A system for the remote detection of gasses as set forth in claim 3, wherein said heat sensor further comprises:
a heat sensor capable of sensing transient molecular relaxation of a laser-stimulated portion of a gas cloud.

19. A system for the remote detection of gasses as set forth in claim 18, wherein said heat sensor further comprises:
a heat sensor capable of sensing transient molecular relaxation occurring on the order of microseconds.

20. A system for the remote detection of gasses as set forth in claim 3, wherein said heat sensor further comprises:
a heat sensor capable of sensing a higher temperature in a portion of said gas cloud illuminated by said laser.

21. A system for the remote detection of gasses as set forth in claim 3, further comprising:
said laser tunable to a sufficient plurality of wavelengths to discriminate target gasses against interferents, said laser illuminating said gas cloud with said plurality of wavelengths and with separate illuminations for each wavelength; and
said heat sensor capable of sensing transient molecular relaxation of a laser-stimulated portion of a gas cloud for each of said separate illuminations.

22. A system for the remote detection of gasses as set forth in claim 21, further comprising:
said separate illuminations selected from the group consisting of illuminations separated by intervals of time, illuminations sequentially transmitted in a continuous manner, and combinations thereof.

\* \* \* \* \*